(12) United States Patent
Smith et al.

(10) Patent No.: US 12,378,178 B2
(45) Date of Patent: Aug. 5, 2025

(54) OLEIC ACID DERIVATIVES AS TREATMENTS FOR FRIEDREICH ATAXIA AND INHIBITORS OF FERROPTOSIS

(71) Applicants: THE TRUSTEES OF THE UNIVERSITY OF PENNSYLVANIA, Philadelphia, PA (US); The Children's Hospital of Philadelphia, Philadelphia, PA (US)

(72) Inventors: Amos Smith, Merion, PA (US); Robert B. Wilson, Wynnewood, PA (US); Donna M Huryn, Allentown, NJ (US); Maria Grazia Cotticelli, Philadelphia, PA (US); Shujuan Xia, Media, PA (US); Taehee Lee, Philadelphia, PA (US); Roberto Forestieri, San Antonio, TX (US)

(73) Assignees: THE TRUSTEES OF THE UNIVERSITY OF PENNSYLVANIA, Philadelphia, PA (US); THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 676 days.

(21) Appl. No.: 17/776,222

(22) PCT Filed: Nov. 12, 2020

(86) PCT No.: PCT/US2020/060195
§ 371 (c)(1),
(2) Date: May 11, 2022

(87) PCT Pub. No.: WO2021/097069
PCT Pub. Date: May 20, 2021

(65) Prior Publication Data
US 2023/0023267 A1    Jan. 26, 2023

Related U.S. Application Data

(60) Provisional application No. 62/934,378, filed on Nov. 12, 2019.

(51) Int. Cl.
C07C 33/42    (2006.01)
A61P 25/14    (2006.01)
C07C 49/227   (2006.01)

(52) U.S. Cl.
CPC ............ *C07C 33/423* (2013.01); *A61P 25/14* (2018.01); *C07C 49/227* (2013.01)

(58) Field of Classification Search
CPC ........ A61P 25/14; A61P 25/00; C07C 33/423; C07C 49/227
See application file for complete search history.

(56) References Cited

U.S. PATENT DOCUMENTS 6,096,784 A      8/2000   Lerner et al.
2008/0103209 A1  5/2008   Piomelli et al.

OTHER PUBLICATIONS

Buchwald et al., "Long-term, continuous intravenous heparin administration by an implantable infusion pump in ambulatory patients with recurrent venous thrombosis." Surgery 88.4 (1980): 507-516.
Goodson, "Medical Applications of Controlled Release." vol. 2, pp. 115-138 (1984).
International Preliminary Report on Patentability from PCT/US2020/060195 dated May 27, 2022.
International Search Report from PCT/US2020/060195 dated Mar. 18, 2021.
Langer, Robert. "New methods of drug delivery." Science 249.4976 (1990): 1527-1533.
Saudek et al., "A preliminary trial of the programmable implantable medication system for insulin delivery." New England Journal of Medicine 321.9 (1989): 574-579.
Sefton et al., "Implantable pumps." Critical Reviews in Biomedical Engineering 14.3 (1987): 201-240.
PUBCHEM-CID: 88095750 Create Date: Feb. 12, 2015 (Feb. 12, 2015) pp. 1-9; p. 2.
PUBCHEM-CID: 89159878 Create Date: Feb. 13, 2015 (Feb. 13, 2015) pp. 1-8; p. 2.

*Primary Examiner* — Sahar Javanmard
(74) *Attorney, Agent, or Firm* — Mark S. Cohen; PEARL COHEN ZEDEK LATZER BARATZ LLP

(57) ABSTRACT

The invention relates to compounds of Formula I or Formula II: to compositions comprising such compounds, and to methods of use thereof for treating neurodegenerative disorders, such as Friedreich ataxia.

16 Claims, 6 Drawing Sheets

OLEIC ACID DERIVATIVES AS TREATMENTS FOR FRIEDREICH ATAXIA AND INHIBITORS OF FERROPTOSIS

CROSS-REFERENCE TO RELATED APPLICATIONS

This application is a National Phase Application of PCT International Application No. PCT/US20/60195, International Filing Date Nov. 12, 2020, claiming the benefit of U.S. Patent Application(s) No(s). 62/934,378, filed Nov. 12, 2019, which is hereby incorporated by reference.

FIELD OF THE INVENTION

The invention relates to compounds of Formula I or Formula II:

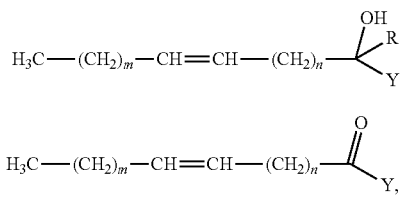

to compositions comprising such compounds, and to methods of use thereof for treating neurodegenerative disorders, such as Friedreich ataxia, and for inhibiting ferroptosis.

BACKGROUND OF THE INVENTION

Friedreich ataxia (FRDA) is an autosomal recessive neuro- and cardio-degenerative disorder characterized by progressive gait and limb ataxia, dysarthria, areflexia, and sensory loss associated with lesions in dorsal root ganglia, corticospinal tracts, and dentate nuclei. In most patients, hypertrophic cardiomyopathy is present. The "hypoplasia and atrophy" of the dorsal root ganglia has been reported and the disease neuropathology has been described extensively.

FRDA is the most common inherited ataxia, with a birth incidence of approximately 1 in 40,000. FRDA onset is generally in the first decade of life and patients are usually wheelchair bound by their twenties and have a shortened life expectancy. Currently there is no cure or FDA approved treatment available for FRDA patients. The disease is caused, in the majority of cases, by a triplet repeat expansion in the first intron of both alleles of the gene encoding the protein frataxin. The triplet repeat expansions lead to decreased frataxin expression through hetero-chromatization. (In a small percentage of cases, the repeat expansion on one allele is accompanied by a point mutation on the second allele, which usually also leads to decreased frataxin levels due to protein instability.) Frataxin is imported into the mitochondria where it functions in the biogenesis of iron sulfur clusters (ISCs), which are prosthetic groups found in many proteins across all cell compartments. Impaired ISC biogenesis leads to mitochondrial iron accumulation and impinges on many cellular processes, including, but not limited to, mitochondrial respiration.

Recently, studies have linked neurodegeneration to ferroptosis, a newly described pathway that can be triggered by iron overload and that leads to cell death through lipid peroxidation. Lipid peroxides can be generated through the Fenton reaction, or enzymatically by lipoxygenases, and are reduced by glutathione-dependent lipid peroxidase, keeping the total level of lipid peroxides tightly regulated; perturbations of this equilibrium can result in a catastrophic rise in lipid peroxidation, leading to ferroptotic cell death. Recently, ferroptosis activation in cellular models of FRDA has been reported and it was shown that primary human FRDA fibroblasts, as well as mouse cell lines containing a disease-associated missense mutation in frataxin, are sensitive to erastin and RSL-3, both known inducers of ferroptosis. It was found that primary fibroblasts derived from individuals with FRDA are unusually sensitive to treatment with a combination of ferric ammonium citrate (FAC) and L-buthionine (S,R)-sulfoximine (BSO), which inhibits the rate-limiting step of glutathione synthesis. Similar results were obtained using primary murine fibroblasts harboring human frataxin with the disease-associated I154F point mutation. Using the FAC+BSO models, it was shown that lipid peroxidation precedes activation of apoptosis.

Known ferroptosis inhibitors, as well as deuterated polyunsaturated fatty acids (D-PUFAs), were efficacious in rescuing the viability of FRDA cells treated with FAC+BSO, highlighting the role of lipid peroxidation in the cellular death caused by these well-studied stressors of FRDA cells. Polyunsaturated fatty acids such as arachidonic acid (C20:4) and linoleic acid (C18:2) were identified as the class of lipids that drives ferroptosis. It was also reported that the monounsaturated oleic acid (C18:1) was a ferroptosis suppressor. Oleic acid is attractive to consider as a therapeutic for FRDA. In addition to the aforementioned role in ferroptosis, oleic acid has been reported to bind directly to the peroxisome proliferator-activated receptor (PPAR) gamma, thereby promoting the expression of PGC1-alpha, a master regulator of mitochondrial biogenesis that is paradoxically down-regulated in FRDA. Oleic acid is also an allosteric inhibitor of soybean and human lipoxygenases (ALOX15). Inhibition of lipoxygenases would be expected to be beneficial to FRDA cells by decreasing the load of lipid peroxides. "Naked" fatty acids, however, can carry with them certain liabilities as therapeutics, particularly because the carboxyl group leads to rapid clearance.

There remains a need in the art for improved therapies, including more effective compounds and methods of using such compounds, for treating various disorders, particularly neurodegenerative diseases.

SUMMARY OF THE INVENTION

In one embodiment, provided herein is a compound represented by Formula I or Formula II

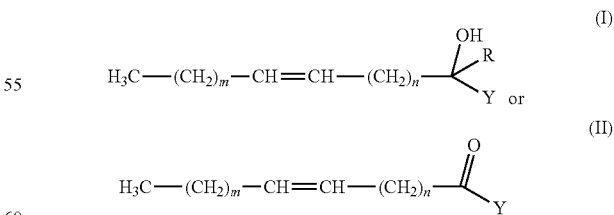

wherein
R is H or $C_1$-$C_6$ alkyl;
m is an integer from 1 to 10;
n is an integer from 1 to 10; and
Y is $CF_3$ or $CCl_3$,
or a prodrug or optical isomer thereof.

In an embodiment, provided herein is a pharmaceutical composition comprising a compound represented by Formula I or Formula II

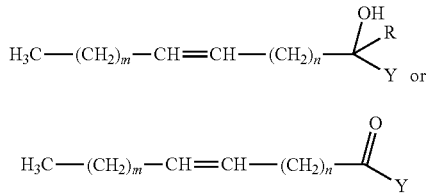

wherein
R is H or $C_1$-$C_6$ alkyl;
m is an integer from 1 to 10;
n is an integer from 1 to 10;
Y is $CF_3$ or $CCl_3$; and
a pharmaceutically acceptable carrier.

In an embodiment, provided herein is a method of treating a neurodegenerative disease in a subject, comprising administering to the subject an effective amount of a compound of Formula I or Formula II, or a pharmaceutical composition thereof:

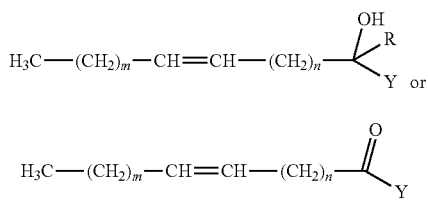

wherein
R is H or $C_1$-$C_6$ alkyl;
m is an integer from 1 to 10;
n is an integer from 1 to 10; and
Y is $CF_3$ or $CCl_3$.

In an embodiment, provided herein is a method of treating Friedreich ataxia in a subject, comprising administering to the subject an effective amount of a compound having the following formula:

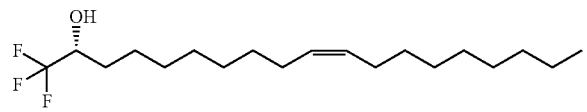

or a pharmaceutical composition thereof.

In an embodiment, provided herein is a method of inhibiting ferroptosis in a subject comprising administering to the subject an effective amount of a compound of Formula I or Formula II, or a pharmaceutical composition thereof:

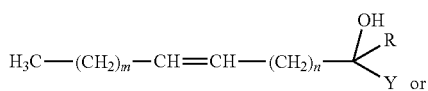

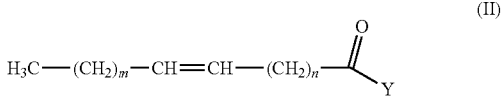

wherein
R is H or $C_1$-$C_6$ alkyl;
m is an integer from 1 to 10;
n is an integer from 1 to 10; and
Y is $CF_3$ or $CCl_3$.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 2A), OA200R was tested to determine whether it could rescue human FRDA fibroblast 3816 treated with erastin. Treatment with erastin at 5 µM resulted in 32% cell survival after 48 h. Addition of OA200R at 5 µM was sufficient to increase survival to 50% (1.5 fold) and at 10 µM and 20 µM survival went up to 80 and 84% (2.5 and 2.6 fold) respectively (FIG. 2B). The S-isomer showed no activity between 20 and 5 µM. In a parallel experiment, OA raised survival to 1.5 fold when used at 20 µM, consistent with the data shown in FIG. 2A. The experiment was repeated at a different time point: treatment with 10 microM erastin for 24 resulted in 85% cell death. Under these conditions, oleic acid at 40 UM did not rescue cell viability whereas OA200R increased survival to 48% at 5 UM and 87% and 88% when used at 10 or 20 UM, respectively. The S-isomer again was inactive at any concentration (FIG. 2C).

(FIG. 3B).

DETAILED DESCRIPTION OF THE INVENTION

Figure 1:
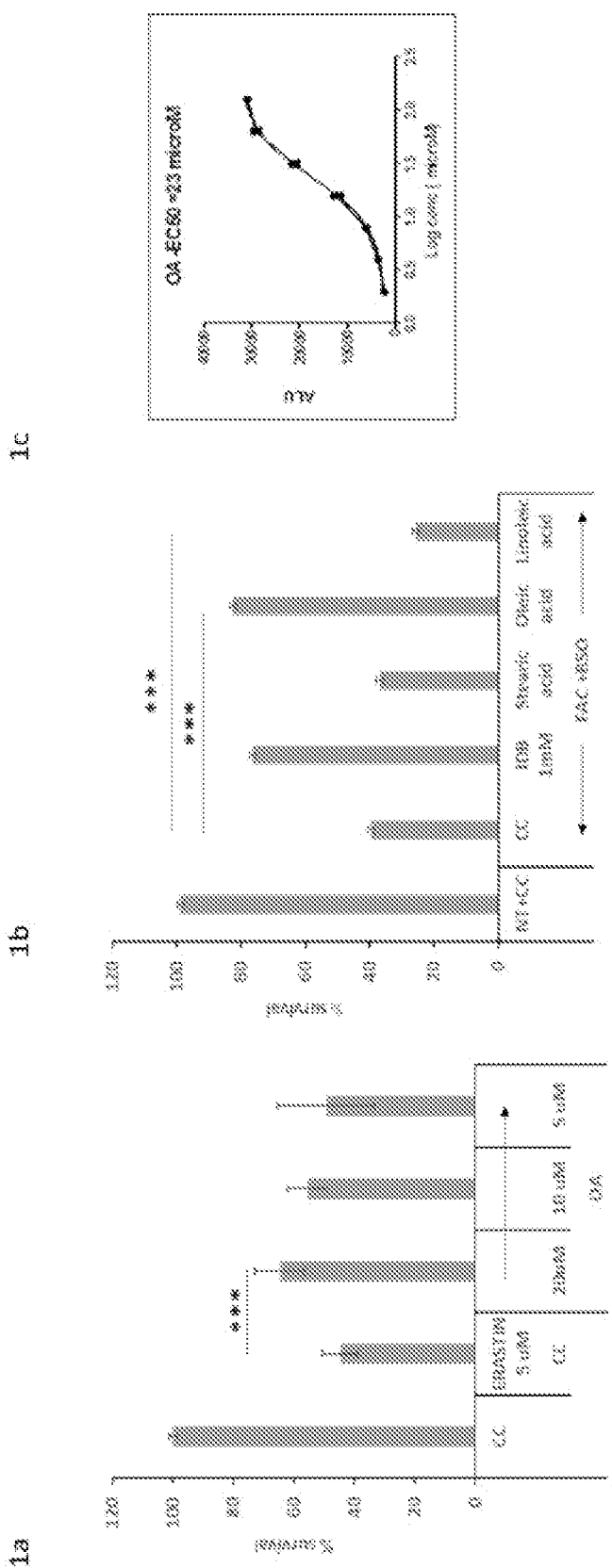
FIG. 1. Oleic acid (OA) was tested to determine whether it could rescue FRDA cells from erastin-induced ferroptosis using the murine 1154F fibroblast model. Treatment with 5 µM erastin for 48 h resulted in 44% cell survival, Oleic acid at 20 µM, 10 µM and 5 µM increased survival in a dose-dependent manner to 65%, 55% and 49% respectively (FIG. 1A). OA was then tested to determine whether it was efficacious in rescuing murine 1154F fibroblasts treated with FAC+BSO. Treatment with FAC+BSO decreased cell viability to 40% of control cells (FIG. 1B), Adding 16 µM linoleic acid further decreased cell viability to 30% of control cells, whereas oleic acid at the same concentration doubled cell survival. Stearic acid (C18:0) had no effect. Oleic Acid—The $EC_{50}$ of oleic acid in the FAC+BSO in mouse fibroblasts assay was 23 µM (FIG. 1C).

The subject matter here may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with this application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In this disclosure, the singular forms "a," "an," and "the" include the plural reference, and reference to a particular numerical value includes at least that particular value, unless context clearly indicates otherwise. Thus, for example, a reference to "a compound" is a reference to one or more such compounds and equivalents thereof known to those skilled in the art, and so forth. As used herein, the term "plurality" means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of this present disclosure, by "about" a certain amount it is meant that the amount is within ±20% of the stated amount, or preferably within ±10% of the stated amount, or more preferably within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e. where the disease or condition does not worsen), delay or slow the progression of a disease or condition, amelioration or palliation of a disease or condition, and remission (whether partial or total) of a disease or condition, whether detectable or undetectable. Those in need of treatment include those already with a disease or condition, as well as those prone to having the disease or condition or those in which the disease or condition is to be prevented.

As used herein, the terms "composition," "formulation," "composition of compounds," "compound," "drug," "pharmacologically active agent," "active agent," "therapeutic," "therapy," "treatment," or "medicament" are used interchangeably, as context dictates, to refer to a compound or compounds or composition of matter which, when administered to a subject (human or animal) induces a desired pharmacological and/or physiologic effect by local and/or systemic action.

The terms "subject," "individual," and "patient" are used interchangeably herein, and refer to an animal, for example a human, to whom treatment with a pharmaceutical composition in accordance with embodiments described herein, is provided. The term "subject" as used herein refers to human and non-human animals. The terms "non-human animals" and "non-human mammals" are used interchangeably herein and include all vertebrates, e.g., mammals, such as non-human primates (particularly higher primates), sheep, dog, rodent (e.g. mouse or rat), guinea pig, goat, pig, cat, rabbits, cows, horses and non-mammals such as reptiles, amphibians, chickens, and turkeys. The formulations described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment, the human is a child According to any of the methods described herein and in one embodiment, the subject is human. In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug or compound or composition (or combination thereof) is said herein to be "indicated" are not restricted to conditions and disorders for which that drug or compound or composition has been expressly approved by a regulatory authority, but also include other conditions and disorders known or reasonably believed by a physician to be amenable to treatment with that drug or compound or composition or combination thereof.

In an embodiment, provided herein is a compound represented by Formula I or Formula II

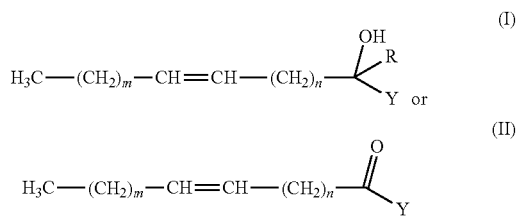

wherein
R is H or $C_1$-$C_6$ alkyl;
m is an integer from 1 to 10;
n is an integer from 1 to 10; and
Y is $CF_3$ or $CCl_3$,
or a prodrug or optical isomer thereof.

In an embodiment, m is an integer from 3 to 8. In another embodiment, n is an integer from 3 to 8. In another embodiment, Y is $CF_3$. In another embodiment, R is H. In another embodiment, R is $CH_3$ or $CH_3CH_2$.

In an embodiment, the compound is represented by Formula IA

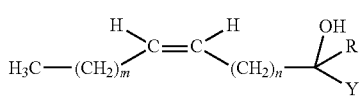
(IA)

In another embodiment, the compound is represented by Formula IB

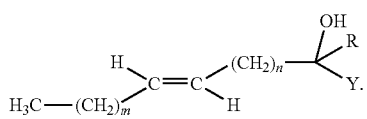
(IB)

In embodiments, the compounds described hereinabove have an S configuration. In other embodiments, the compounds have an R configuration.

In an embodiment, the weight ratio of the R isomer to the S isomer is from 70:30 to 99.99:0.01. In other embodiments, the weight ratio of the R isomer to the S isomer is 70:30, or 75:25, or 80:20, or 85:15, or 90:10, or 95:5, or 98:2, or 99:1, or 99.99:0.01.

In an embodiment, the weight ratio of the S isomer to the R isomer is from 70:30 to 99.99:0.01. In other embodiments, the weight ratio of the S isomer to the R isomer is 70:30, or 75:25, or 80:20, or 85:15, or 90:10, or 95:5, or 98:2, or 99:1, or 99.99:0.01.

In an embodiment, the compound is a racemic mixture.

In another embodiment, the compound is represented by Formula IIA

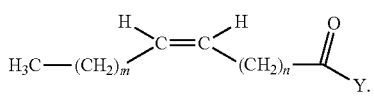
(IIA)

In another embodiment, the compound is represented by Formula IIB

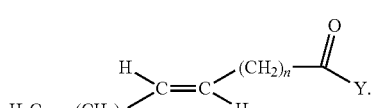
(IIB)

In some embodiments, the compound is selected from

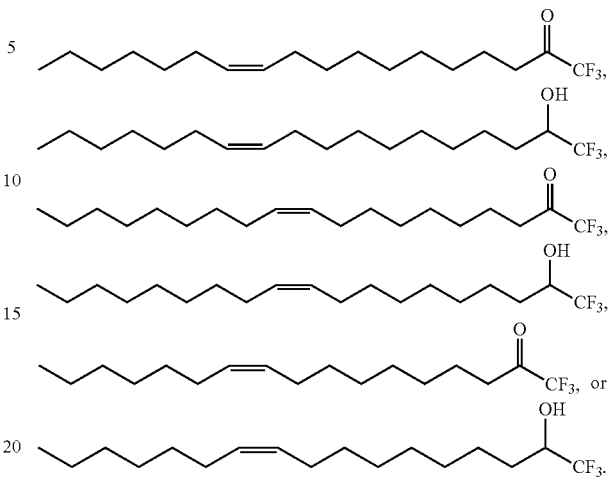

In an embodiment, the compound is

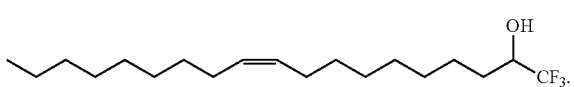

In an embodiment, the compound is

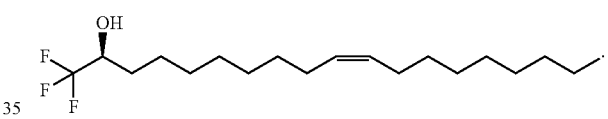

In an embodiment, the compound is

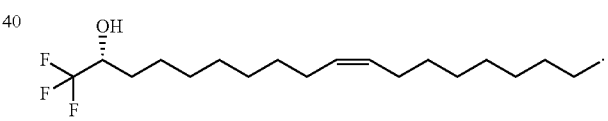

In an embodiment, provided herein is a pharmaceutical composition comprising a compound represented by Formula I or Formula II

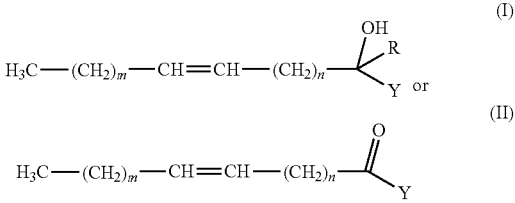
(I)

(II)

wherein
R is H or $C_1$-$C_6$ alkyl;
m is an integer from 1 to 10;
n is an integer from 1 to 10;
Y is $CF_3$ or $CCl_3$; and
a pharmaceutically acceptable carrier.

In an embodiment, m is an integer from 3 to 8. In another embodiment, n is an integer from 3 to 8. In another embodiment, Y is $CF_3$. In another embodiment, R is H. In other embodiments, R is $CF_3$ or $CH_3CH_2$.

In another embodiment, the compound is represented by Formula IA

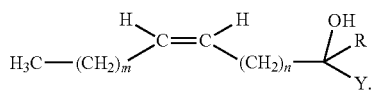
(IA)

In another embodiment, the compound is represented by Formula IB

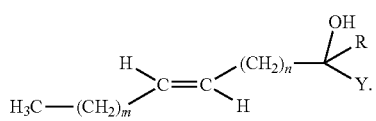
(IB)

In an embodiment, the compound has an S configuration. In another embodiment, the compound has an R configuration.

In an embodiment, the weight ratio of the R isomer to the S isomer is from 70:30 to 99.99:0.01. In other embodiments, the weight ratio of the R isomer to the S isomer is 70:30, or 75:25, or 80:20, or 85:15, or 90:10, or 95:5, or 98:2, or 99:1, or 99.99:0.01.

In an embodiment, the weight ratio of the S isomer to the R isomer is from 70:30 to 99.99:0.01. In other embodiments, the weight ratio of the S isomer to the R isomer is 70:30, or 75:25, or 80:20, or 85:15, or 90:10, or 95:5, or 98:2, or 99:1, or 99.99:0.01.

In an embodiment, the compound is a racemic mixture.

In an embodiment, the compound is represented by Formula IIA

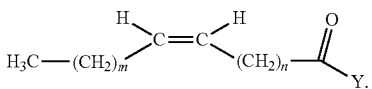
(IIA)

In another embodiment, the compound is represented by Formula IIB

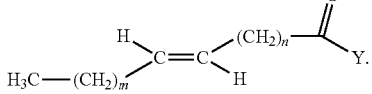
(IIB)

In an embodiment, the compound is

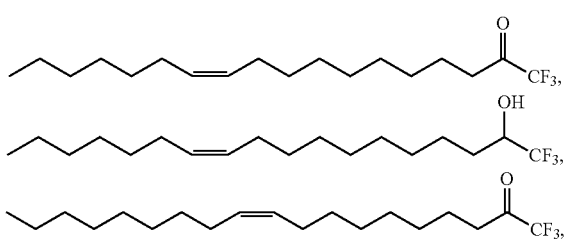

-continued

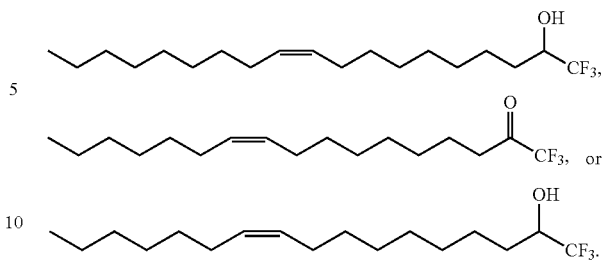

In an embodiment, the compound is (structure: alkenyl chain with C(=O)CF₃)

In an embodiment, the compound is (structure: F₃C-CH(OH)-alkenyl chain, S configuration)

In an embodiment, the compound is (structure: F₃C-CH(OH)-alkenyl chain, S configuration)

In an embodiment, provided herein is a method of treating a neurodegenerative disease in a subject, comprising administering to the subject an effective amount of a compound of Formula I or Formula II, or a pharmaceutical composition thereof:

$$H_3C-(CH_2)_m-CH=CH-(CH_2)_n-\overset{OH}{\underset{Y}{C}}\overset{R}{\phantom{C}}$$ (I)

or $$H_3C-(CH_2)_m-CH=CH-(CH_2)_n-\overset{O}{C}-Y$$ (II)

wherein

R is H or $C_1$-$C_6$ alkyl;

m is an integer from 1 to 10;

n is an integer from 1 to 10; and

Y is $CF_3$ or $CCl_3$.

In an embodiment, m is an integer from 3 to 8. In n embodiment, n is an integer from 3 to 8. In an embodiment, Y is $CF_3$. In an embodiment, R is H. In an embodiment, R is $CH_3$ or $CH_3CH_2$.

In an embodiment, the compound is represented by Formula IA

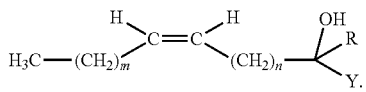
(IA)

In another embodiment, the compound is represented by Formula IB

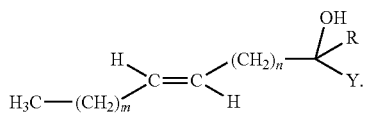
(IB)

In an embodiment, the compound has an S configuration. In another embodiment, the compound has an R configuration.

In an embodiment, the weight ratio of the R isomer to the S isomer is from 70:30 to 99.99:0.01. In other embodiments, the weight ratio of the R isomer to the S isomer is 70:30, or 75:25, or 80:20, or 85:15, or 90:10, or 95:5, or 98:2, or 99:1, or 99.99:0.01.

In an embodiment, the weight ratio of the S isomer to the R isomer is from 70:30 to 99.99:0.01. In other embodiments, the weight ratio of the S isomer to the R isomer is 70:30, or 75:25, or 80:20, or 85:15, or 90:10, or 95:5, or 98:2, or 99:1, or 99.99:0.01.

In an embodiment, the compound is a racemic mixture.

In an embodiment, the compound is represented by Formula IIA

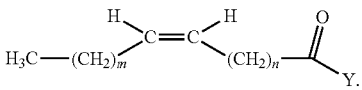
(IIA)

In an embodiment, the compound is represented by Formula IIB

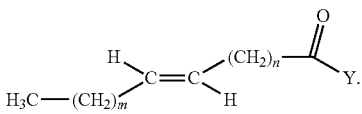
(IIB)

In an embodiment, the compound is

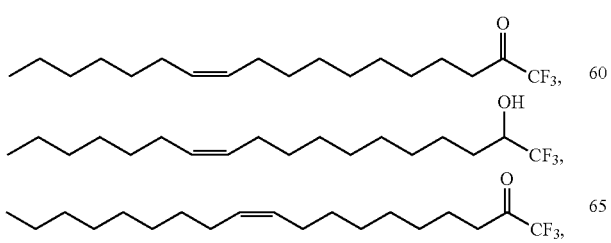

In an embodiment, the compound is

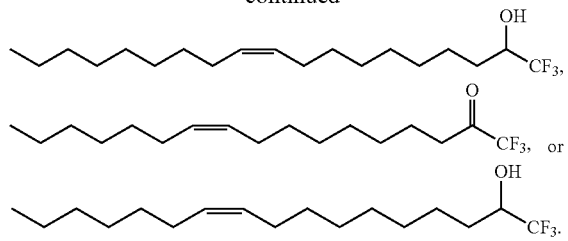

In an embodiment, the compound is

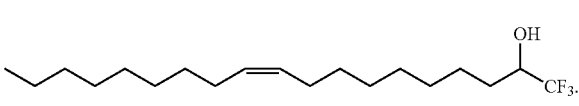

In an embodiment, the compound is

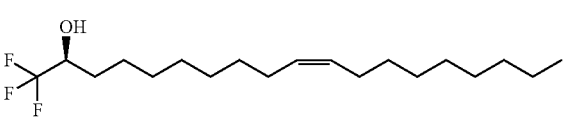

In an embodiment, the compound is

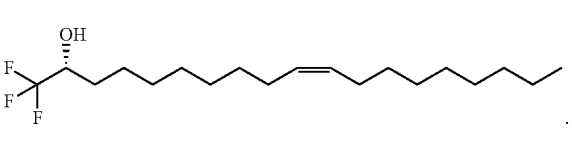

In an embodiment, the neurodegenerative disease is Friedreich ataxia, Parkinson's disease, Huntingdon's disease, or Alzheimer's disease.

In an embodiment, provided herein is a method of treating Friedreich ataxia in a subject, comprising administering to the subject an effective amount of a compound having the following formula:

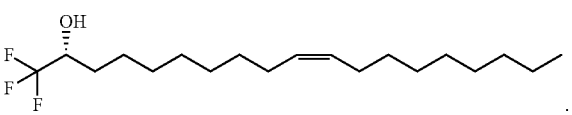

or a pharmaceutical composition thereof.

In an embodiment, provided herein is a method of inhibiting ferroptosis in a subject, comprising administering to the subject an effective amount of a compound of Formula I or Formula II, or a pharmaceutical composition thereof:

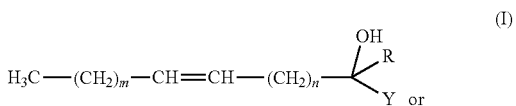
(I)

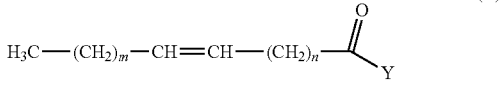
(II)

wherein

R is H or $C_1$-$C_6$ alkyl;

m is an integer from 1 to 10;

n is an integer from 1 to 10; and

Y is $CF_3$ or $CCl_3$.

In an embodiment, m is an integer from 3 to 8. In another embodiment, n is an integer from 3 to 8. In an embodiment, Y is $CF_3$. In an embodiment, R is H. In another embodiment, R is $CH_3$ or $CH_3CH_2$.

In an embodiment, the compound is represented by Formula IA $$\text{(IA)}$$

$$H_3C-(CH_2)_m \overset{H}{\underset{}{\text{C}}}=\overset{H}{\underset{}{\text{C}}}-(CH_2)_n-\underset{Y}{\overset{OH}{\underset{|}{C}}}-R$$

In another embodiment, the compound is represented by Formula IB $$\text{(IB)}$$

$$H_3C-(CH_2)_m \overset{H}{\underset{}{\text{C}}}=\overset{(CH_2)_n}{\underset{H}{\text{C}}}-\underset{Y}{\overset{OH}{\underset{|}{C}}}-R$$

In an embodiment, the compound has an S configuration. In another embodiment, the compound has an R configuration.

In an embodiment, the weight ratio of the R isomer to the S isomer is from 70:30 to 99.99:0.01. In other embodiments, the weight ratio of the R isomer to the S isomer is 70:30, or 75:25, or 80:20, or 85:15, or 90:10, or 95:5, or 98:2, or 99:1, or 99.99:0.01.

In an embodiment, the weight ratio of the S isomer to the R isomer is from 70:30 to 99.99:0.01. In other embodiments, the weight ratio of the S isomer to the R isomer is 70:30, or 75:25, or 80:20, or 85:15, or 90:10, or 95:5, or 98:2, or 99:1, or 99.99:0.01.

In an embodiment, the compound is a racemic mixture.

In an embodiment, the compound is represented by Formula IIA $$\text{(IIA)}$$

$$H_3C-(CH_2)_m \overset{H}{\underset{}{\text{C}}}=\overset{H}{\underset{}{\text{C}}}-(CH_2)_n-\overset{O}{\underset{}{\text{C}}}-Y$$

In an embodiment, the compound is represented by Formula IIB $$\text{(IIB)}$$

$$H_3C-(CH_2)_m \overset{H}{\underset{}{\text{C}}}=\overset{(CH_2)_n}{\underset{H}{\text{C}}}-\overset{O}{\underset{}{\text{C}}}-Y$$

In an embodiment, the compound is

[Structures showing various trifluoromethyl ketone and alcohol compounds with alkenyl chains]

In an embodiment, the compound is

[Structure of an alkenyl trifluoromethyl carbinol]

In an embodiment, the compound is

[Structure with OH and $CF_3$ group on chiral carbon with alkenyl chain]

In an embodiment, the compound is

[Structure with OH and $CF_3$ group on chiral carbon with alkenyl chain]

In certain embodiments of the methods described herein, the subject has Friedreich ataxia or is at risk of developing Friedreich ataxia. In certain embodiments, the subject has or is at risk of developing a neurodegenerative brain disorder selected from the group consisting of Parkinson's disease, Huntington's disease and Alzheimer's disease. Ferroptosis has been implicated not only in pathological cell death associated with these various degenerative diseases (e.g., Alzheimer's, Huntington's and Parkinson's diseases), but also others, including without limitation, carcinogenesis, stroke, intracerebral hemorrhage, traumatic brain injury, ischemic-reperfusion injury and kidney degeneration. The compounds and compositions described herein are suitable for treating these disorders, as well as other disorders, including but not limited to, diseases in which ferroptosis plays a role and/or in which inhibiting ferroptosis is desired.

In an embodiment, provided herein is a method of treating Friedreich's ataxia in a subject, comprising administering to the subject an effective amount of a compound of Formula I or Formula II, or a pharmaceutical composition thereof:

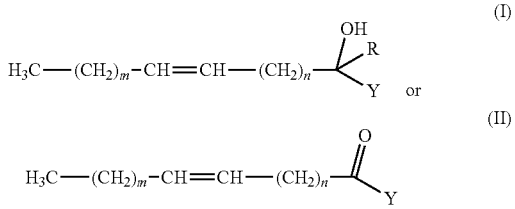

wherein
R is H or C$_1$-C$_6$ alkyl;
m is an integer from 1 to 10;
n is an integer from 1 to 10; and
Y is CF$_3$ or CCl$_3$.
In an embodiment, the compound is:

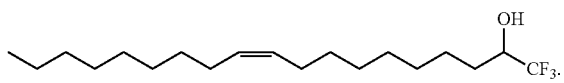 [SMILES: CCCCCCCC/C=C\CCCCCCCC(O)C(F)(F)F]

In another embodiment, this compound has an R-configuration.

It is understood that the compounds, as described herein, may be substituted with any number of substituents or functional moieties. In general, the term "substituted" whether preceded by the term "optionally" or not, and substituents contained in the formulas herein, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, permissible substituents include acyclic and cyclic, branched and unbanked, carbocyclic and heterocyclic, aromatic and non-aromatic, carbon and heteroatom substituents of organic compounds. For the purposes described here, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned herein are preferably those that result in formation of stable compounds useful in treating and preventing, for example disorders, as described generally above. Examples of substituents include, but are not limited to aliphatic; heteroaliphatic; alicyclic; heterocyclic; aromatic, heteroaromatic; aryl; heteroaryl; alkylaryl; aralkyl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CH$_2$CF$_3$; —CHCl$_2$; CH$_2$OH; —CH$_2$CH$_2$OH; —CF$_2$NH$_2$; —CH$_2$SO$_2$CH$_3$; or -GR$^{G1}$ where G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O) NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(NR$^{G2}$)—, —NR$^{G2}$C (=NR$^{G3}$)—, —NR$^{G2}$SO$_2$—, —NR$^{G2}$SO$_2$NR$^{G3}$—, or —SO$_2$NR$^{G2}$—, where each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons as defined by IUPAC, which are optionally substituted with one or more functional groups. As defined herein, "aliphatic" is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. As used herein, "lower alkyl" is used to indicate those alkyl groups (substituted, unsubstituted, branched or unbranched) having about 1-6 carbon atoms. In some instances, aliphatic can include alicyclic or cycloalkyl, including unsaturations therein.

In certain embodiments, the alkyl, alkenyl and alkynyl groups employed herein contain 1-20; 2-20; 3-20; 4-20; 5-20; 6-20; 7-20 or 8-20 aliphatic carbon atoms. In certain other embodiments, the alkyl, alkenyl, and alkynyl groups employed herein contain 1-10; 2-10; 3-10; 4-10; 5-10; 6-10; 7-10 or 8-10 aliphatic carbon atoms. In yet other embodiments, the alkyl, alkenyl, and alkynyl groups employed herein contain 1-8; 2-8; 3-8; 4-8; 5-8; 6-20 or 7-8 aliphatic carbon atoms. In still other embodiments, the alkyl, alkenyl, and alkynyl groups employed herein contain 1-6; 2-6; 3-6; 4-6 or 5-6 aliphatic carbon atoms. In yet other embodiments, the alkyl, alkenyl, and alkynyl groups employed herein contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

As used herein, the term "alicyclic" refers to compounds that combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups, Illustrative alicyclic groups thus include, but are not limited to, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

As used herein, the term "cycloalkyl" refers to cyclic alkyl groups, specifically to groups having three to seven, preferably three to ten carbon atoms. Suitable cycloalkyls include, but are not limited to, cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

As used herein, the term "heteroaliphatic" refers to aliphatic moieties in which one or more carbon atoms in the main chain have been replaced with a heteroatom. Thus, a heteroaliphatic group refers to an aliphatic chain which contains one or more oxygen, sulfur, nitrogen, phosphorus or silicon atoms in place of carbon atoms in the aliphatic main chain. Heteroaliphatic moieties may be branched or linear unbranched. In certain instances, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—; —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

As used herein, the term "heteroalicyclic", "heterocycloalkyl" or "heterocyclic" refers to compounds which combine properties of heteroaliphatic and cyclic compounds and include, but are not limited to, saturated and unsaturated mono- or polycyclic ring systems having 5-16 atoms wherein at least one ring atom is a heteroatom selected from O, S and N (wherein the nitrogen and sulfur heteroatoms may optionally be oxidized), where the ring systems are optionally substituted with one or more functional groups, as defined herein. In certain instances, the term "heterocyclic" refers to a non-aromatic 5-, 6- or 7-membered ring or polycyclic group, including, but not limited to, a bi- or tri-cyclic group comprising fused six-membered rings having between one and three heteroatoms independently selected from oxygen, sulfur and nitrogen, where (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, piperidinyl, piperazinyl, oxazolidinyl, isoxazolidinyl, morpholinyl, thiazolidinyl, isothiazolidinyl, and tetrahydrofuryl. In certain instances, a "substituted heterocycloalkyl or heterocycle" group is utilized and as used herein, refers to a heterocycloalkyl or heterocycle group, as defined above, substituted by the independent replacement of one or more hydrogen atoms thereon with aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)—, —$NR^{G2}$C(=O)$NR^{G2}$—, —C(=S)—; —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety.

Additionally, it will be appreciated that any of the alicyclic or heterocyclic moieties described above and herein may comprise an aryl or heteroaryl moiety fused thereto.

In general, as used herein, the term "aromatic moiety" refers to a stable mono- or polycyclic, unsaturated moiety having preferably 3-14 carbon atoms, each of which may be substituted or unsubstituted. In certain instances, the term "aromatic moiety" refers to a planar ring having p-orbitals perpendicular to the plane of the ring at each ring atom and satisfying the Huckel rule where the number of pi electrons in the ring is (4n+2) wherein n is an integer, A mono- or polycyclic, unsaturated moiety that does not satisfy one or all of these criteria for aromaticity is defined herein as "non-aromatic," and is encompassed by the term "alicyclic". Examples of aromatic moieties include, but are not limited to, phenyl, indanyl, indenyl, naphthyl, phenanthryl and anthracyl.

In general, as used herein, the term "heteroaromatic moiety" refers to stable substituted or unsubstituted unsaturated mono-heterocyclic or polyheterocyclic moieties having preferably 3-14 carbon atoms, comprising at least one ring having p-orbitals perpendicular to the plane of the ring at each ring atom, and satisfying the Huckel rule where the number of pi electrons in the ring is (4n+2) wherein n is an integer. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic) aromatic, -(heteroaliphatic)aromatic, -(aliphatic)heteroaromatic, -(heteroaliphatic) heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkylaromatic, -(heteroalkyl)aromatic, -(heteroalkyl)heteroaromatic, and -(heteroalkyl)heteroaromatic" are interchangeable. In some instances, corresponding moieties may be referred to synonymously as aralkyl, heteroaralkyl and the like, Substituents include, but are not limited to, any of the previously mentioned substituents, i.e., the substituents recited for aliphatic moieties, or for other moieties as disclosed herein, resulting in the formation of a stable compound.

"Aralkyl," also called "arylalkyl," refers to an aryl group terminating with an aliphatic group, such as a benzyl, phenylethyl, phenylpropyl, or phenylbutyl group, etc. The aryl moiety may be substituted as generally described herein, as may be the aliphatic moiety. The aliphatic moiety may be as defined above, such as an alkyl, alkenyl or alkynyl group.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain instances, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As defined herein, "aryl" and "heteroaryl" groups (including bicyclic aryl groups) can be unsubstituted or substituted, wherein substitution includes replacement of one or more of the hydrogen atoms thereon independently with any of the previously mentioned substituents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, where substitution includes replacing one or more of the hydrogen atoms thereon independently with any one or more of the following moieties including, but not limited to: aliphatic; heteroaliphatic; alicyclic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, OC(=O)O—; —OC(=O)$NR^{G2}$—, —$NR^{G2}$C(=O)O—, —$NR^{G2}$C(=O)$NR^{G2}$—; —C(=S)S—, —C(=S)S—, —SC(=S)—, —SC(=S)S—; —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, $NR^{G2}SO_2$—, —$NR^{G2}SO_2NR^{G3}$—, or —$SO_2NR^{G2}$—, where each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic; aromatic, heteroaromatic, aryl, heteroaryl, alkylaryl, or alkylheteroaryl moiety. It will also be appreciated, that any two adjacent groups taken together may represent a 4, 5, 6 or 7-membered substituted or unsubstituted alicyclic or heterocyclic moiety.

As used herein, the term "alkoxy" or "alkyloxy" refers to a saturated (i.e., O-alkyl) or unsaturated (i.e., O-alkenyl and O-alkynyl) group attached to the parent molecular moiety through an oxygen atom. In certain instances, the alkyl group contains 1-20; 2-20; 3-20; 4-20; 5-20; 6-20; 7-20 or 8-20 aliphatic carbon atoms. In certain other instances; the alkyl group contains 1-10; 2-10; 3-10; 4-10; 5-10; 6-10; 7-10 or 8-10 aliphatic carbon atoms. In yet other instances, the alkyl, alkenyl, and alkynyl groups employed in the invention contain 1-8; 2-8; 3-8; 4-8; 5-8; 6-20 or 7-8 aliphatic carbon atoms. In still other instances; the alkyl group contains 1-6; 2-6; 3-6; 4-6 or 5-6 aliphatic carbon atoms. In yet other instances, the alkyl group contains 1-4; 2-4 or 3-4 aliphatic carbon atoms, Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

As used herein, the term "thioalkyl" refers to a saturated (i.e. S-alkyl) or unsaturated (i.e. S-alkenyl and S-alkynyl) group attached to the parent molecular moiety through a sulfur atom. In certain instances, the alkyl group contains 1-20 aliphatic carbon atoms. In certain other instances, the alkyl group contains 1-10 aliphatic carbon atoms. In yet other instances, the alkyl, alkenyl, and alkynyl groups employed contain 1-8 aliphatic carbon atoms. In still other instances; the alkyl group contains 1-6 aliphatic carbon atoms. In yet other instances, the alkyl group contains 1-4 aliphatic carbon atoms. Examples of thioalkyl include, but are not limited to, methylthio, ethylthio, propylthio; isopropylthio, n-butylthio, and the like.

The term "alkylamino" refers to a group having the structure —NHR' wherein R' is aliphatic or alicyclic, as defined herein. The term "aminoalkyl" refers to a group having the structure $NH_2R'$—, wherein R' is aliphatic or alicyclic, as defined herein. In certain instances, the aliphatic or alicyclic group contains 1-20 aliphatic carbon atoms. In certain other instances; the aliphatic or alicyclic group contains 1-10 aliphatic carbon atoms. In still other instances, the aliphatic or alicyclic group contains 1-6 aliphatic carbon atoms. In yet other instances, the aliphatic or alicyclic group contains 1-4 aliphatic carbon atoms. In yet other instances, R' is an alkyl, alkenyl; or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds described herein include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N($R_x$)$_2$; —OC(=O)$R_x$; —$OCO_2R_x$; —OC(=O)N($R_x$)$_2$; —N($R_x$)$_2$; —$OR_x$; —$SR_x$; —S(O)$R_x$; —S(O)$_2R_x$; —$NR_x$(CO)$R_x$; —N($R_x$)$CO_2R_x$; —N($R_x$)S(O)$_2R_x$; —N($R_x$)C(=O)N($R_x$)$_2$; —S(O)$_2$N($R_x$)$_2$; wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

As used herein, the term "acyl" refers to a group having the general formula —C(=O)R, where R is an aliphatic, alicyclic, heteroaliphatic, heterocyclic, aromatic or heteroaromatic moiety, as defined herein.

As used herein, the term "C$_{2-6}$ alkenylene" refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and brandied groups. Similar the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

As used herein, the phrase, "pharmaceutically acceptable derivative" denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include, among others, prodrugs. A prodrug is a derivative of a compound, usually with significantly reduced pharmacological activity, which contains an additional moiety, which is susceptible to removal in vivo yielding the parent molecule as the pharmacologically active species. An example of a prodrug is an ester, which is cleaved in vivo to yield a compound of interest. Another example is an N-methyl derivative of a compound, which is susceptible to oxidative metabolism resulting in N-demethylation, Pro-drugs of a variety of compounds, and materials and methods for derivatizing the parent compounds to create the prodrugs, are known and may be adapted to the present invention.

The phrase, "active metabolite", refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, a compound is metabolized to pharmacologically active metabolites.

The term "isomers" refers to stereoisomers and/or diastereomers of the compounds, as some of the foregoing compounds can comprise one or more asymmetric centers, and thus can exist in various isomeric forms. Thus, compounds and pharmaceutical compositions thereof described herein may be in the form of an individual enantiomer, diastereomer or geometric isomer, or may be in the form of a mixture of stereoisomers. In certain instances, the compounds are enantiopure compounds. In certain other instances, mixtures of stereoisomers or diastereomers are provided. In other instances, a compound is racemic.

The term "geometrical isomers" refers to cis-trans isomerism, syn-anti or E/Z isomerism based on the Cahn-Ingold-Prelog system. See March's Advanced Organic Chemistry: Reactions, Mechanisms and Structures, Sixth Edition, Wiley-Interscience, pages 182-195 (2007), The term "geometrical isomers" as used herein, refers to compounds having double bond with an E or Z configuration or cis-trans isomers of monocyclic or fused ring systems.

Furthermore, certain compounds, as described herein may have one or more double bonds that can exist as either the Z or E isomer, unless otherwise indicated. In certain instances, the compounds encompass individual isomers substantially free of other isomers and alternatively, as mixtures of various isomers, e.g., racemic mixtures of stereoisomers. In addition to the above-mentioned compounds per se, also encompassed herein are pharmaceutically acceptable derivatives of these compounds and compositions comprising one or more of these compounds and one or more pharmaceutically acceptable excipients or additives.

The term "metal chelate" refers to a compound herein that has bound one or more metal ions, such as but not limited to iron or manganese, in any one or more of their ionic forms.

As described herein throughout, Friedreich ataxia (FRDA) is characterized by a progressive neurodegeneration. Most patients develop a cardiomyopathy in which hypertrophy is accompanied by a replacement of cardiomyocytes with fibrotic tissue. The molecular mechanisms leading to cardiomyocyte cell death are incompletely understood.

Ferropotosis is a pathway of regulated, iron-dependent cell death, biochemically distinct from apoptosis, which requires lipid peroxidation. In cells, lipid peroxides can be generated enzymatically or through the Fenton reaction. Lipoxygenase enzymes contribute to the generation of lipid peroxides, which are reduced by glutathione-dependent lipid peroxidase, keeping the total level of lipid peroxides tightly regulated Perturbations of this equilibrium can result in a catastrophic rise in lipid peroxidation, leading to cell death.

Inhibitors of ferroptosis, such as ferrostatins and liproxstatins, protect from ischemic injury in mouse models in the liver, kidney, brain, and heart. These inhibitors are also protective in models of degenerative brain disorders, including Parkinson's, Huntington's, and Alzheimer's diseases, as well as in other forms of neurodegeneration and traumatic and hemorrhagic brain injury. Ferroptosis in some other tissues and diseases has been examined, including liver hemochromatosis. A number of clinicopathological features of dementia are consistent with ferroptosis. Similar features are manifest in other neurodegenerative diseases.

Compounds, Pharmaceutical Compositions and Methods of Administration

Another embodiment herein comprises compounds and pharmaceutical compositions of such compounds useful for the purposes described herein, but not limited thereto.

Pharmaceutical compositions comprising any of the aforementioned compounds and classes and subclasses of special interest are embraced herein.

Embodied herein are compounds as described above and pharmaceutical compositions thereof. It will be appreciated that the compounds and compositions, according to the methods described herein, may be administered using an amount and a route of administration effective for treating conditions or diseases in which inhibiting ferroptosis has a therapeutically useful role. Thus, the expression "effective amount" as used herein, refers to a sufficient amount of agent to inhibit ferroptosis and/or to exhibit a therapeutic effect. The exact amount required will vary from subject to subject, depending on the species, age, and general condition of the subject, the particular therapeutic agent, its mode and/or route of administration, and the like. The compounds described herein are preferably formulated in dosage unit form for ease of administration and uniformity of dosage. The expression "dosage unit form" as used herein refers to a physically discrete unit of therapeutic agent appropriate for a patient to be treated. It will be understood, however, that the total daily usage of the compounds and compositions described herein will be decided by a physician within the scope of sound medical judgment. The specific therapeutically effective dose level for a particular patient or organism will depend upon a variety of factors including the disorder being treated and the severity of the disorder; the activity of the specific compound employed; the specific composition employed; the age, body weight, general health, sex and diet of the patient; the time and route of administration; and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, pharmaceutical compositions described herein can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder treated. In certain embodiments, compounds described herein may be administered at dosages of about 0.001 mg/kg to about 50 mg/kg, preferably from about 0.1 mg/kg to about 10 mg/kg for parenteral administration, or preferably from about 1 mg/kg to about 50 nag/kg, more preferably from about 10 mg/kg to about 50 mg/kg for oral administration, of subject body weight per day, one or more times a day, to obtain a desired therapeutic effect. It will also be appreciated that dosages smaller than 0.001 mg/kg or greater than 50 mg/kg (e.g., 50-100 mg/kg) can be administered to a subject. In certain embodiments, compounds are administered orally or parenterally.

In other embodiments of methods and compositions described herein, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active agent is formulated in a capsule. For these embodiments, the compositions can comprise a hard gelatin capsule, in addition to the active agent and inert carrier or diluent.

In some embodiments, the pharmaceutical compositions are administered by intravenous, intra-arterial, subcutaneous or intra-muscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In some embodiments, the pharmaceutical compositions are administered intra-arterially and formulated in a form suitable for intra-arterial administration. In some embodiments, the pharmaceutical compositions are administered intra-muscularly and formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In some embodiments, the pellet provides for controlled release of active agent over a period of time.

In another embodiment, the active compound is delivered in a vesicle, e.g. a liposome.

In other embodiments, carriers or diluents used in methods described herein include, but are not limited to, a gum, a starch (e.g. corn starch, pregelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like, Examples are sterile liquids such as water and oils, with or without the addition of a surfactant and other pharmaceutically acceptable adjuvants, in general, water, saline, aqueous dextrose and related sugar solutions, and glycols such as propylene glycols or polyethylene glycol are preferred liquid carriers, particularly for injectable solutions, Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g. Tris-HCL, acetate, phosphate) of various pH and ionic strength, additives such as albumin or gelatin to prevent absorption to surfaces, detergents (e.g. Tween 20, Tween 80, Pluronic 168, bile acid salts), protease inhibitors, surfactants (e.g. sodium lauryl sulfate), permeation enhancers, solubilizing agents (e.g. glycerol, polyethylene glycerol), anti-oxidants (e.g. ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g. poloxamers or poloxamines), coating and film forming agents (e.g. ethyl cellulose, acrylates, polymethacrylates) and/or adjuvants.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Sefton, *CRC Crit. Ref. Biomed. Eng.* 14:201 (1987); Buchwald et al., Surgery 88:507 (1980); Saudek et al., *N. Engl. J. Med.* 321:574 (1989). In other embodiments, polymeric materials are used, e.g. in microspheres or an implant. In yet other embodiments, a controlled release system is placed in proximity to a target cell, thus requiring only a fraction of the systemic dose (see, e.g., Goodson, in Medical Applications of Controlled Release, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also included herein are particulate compositions coated with polymers (e.g. poloxamers or poloxamines) and the compound coupled to antibodies directed against tissue-specific receptors, ligands or antigens or coupled to ligands of tissue-specific receptors.

Also comprehended herein are compounds modified by covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. Modified compounds are known to exhibit substantially longer half-lives in blood after intravenous injection than the corresponding unmodified compounds. Such modifications may also increase a compound's solubility in aqueous solution, eliminate aggregation, enhance\physical and chemical stability of the compound, and greatly reduce its immunogenicity and reactivity. As a result, a desired in viva biological activity may be achieved by administering such polymer-compound adducts less frequently or in lower doses than with the unmodified compound.

In one embodiment, the methods described herein comprise administering an active compound as the sole active ingredient. However, also encompassed within the scope of the methods described herein to treat diseases and disorders that comprise administering the active compound in combination with one or more therapeutic agents. In another embodiment, these agents are appropriate for the disease or disorder that is being treated, as is well known in the art.

Some of the foregoing compounds can comprise one or more asymmetric centers, and thus can exist in various isomeric forms, e.g., stereoisomers and/or diastereomers. The compounds and pharmaceutical compositions thereof may be in the form of an individual enantiomer, diastereomer or geometric isomer, or in the form of a mixture of stereoisomers. In some embodiments, the compounds are enantiopure. In other embodiments; mixtures of stereoisomers or diastereomers are provided. In other embodiments, racemic mixtures are provided.

Furthermore, certain compounds, as described herein may have one or more double bonds that can exist as either the Z or E isomer, unless otherwise indicated. The compounds can encompass individual isomers substantially free of other isomers or alternatively; as mixtures of various isomers, e.g., racemic mixtures of stereoisomers. In addition to the above-mentioned compounds per se, also encompassed herein are pharmaceutically acceptable derivatives of these compounds and compositions comprising one or more the compounds and one or more pharmaceutically acceptable excipients or additives.

All patents, patent applications, and scientific publications cited herein are hereby incorporated by reference in their entireties.

The following examples are presented in order to more fully illustrate the preferred embodiments of the invention. It should in no way be construed, however, as limiting the broad scope of the invention.

EXAMPLES

Previous studies suggested that neuronal cell death n FRDA may involve ferroptosis, a regulated, iron-dependent form of cell death involving lipid peroxidation. It has been reported that oleic acid acts as a ferroptosis inhibitor. As reflected in these Examples, oleic acid was found to rescue FRDA cells in cell-viability assays. Oleic acid, other natural fatty acids, and a series of fatty acid analogs, were evaluated in cell-based assays that mimic the Friedreich's ataxia phenotype, to identify potential starting points for FRDA probe and drug discovery efforts.

To investigate these effects further, 25 fatty acid derivatives were tested for their ability to rescue FRDA cells. Twelve were commercially available analogs of oleic acid, or other fatty acids that differed in the number of carbon atoms, site of unsaturation, olefin geometry, and/or degree of unsaturation, and thirteen analogs were synthesized Among these, a novel compound, [rac]-OA-200, was significantly more potent than oleic acid in rescuing cell viability in cells treated with FAC and BSO, or with erastin. Furthermore, separation of the enantiomers of OA-200 led to the identification of a eutomer and a distomer, and indicated that the effects were stereospecific, with the (R)-enantiomer exhibiting seven-fold more potency than the (S)-enantiomer. Data suggest a mechanism consistent with radical trapping antioxidant, albeit a stereoselective one, although a specific molecular target has not yet been identified.

Cell lines commonly used to study FRDA were previously shown to sensitive to erastin and RSL-3, both known inducers of ferroptosis, and, conversely, ferroptosis inhibitors are efficacious in protecting human and mouse cellular models of FRDA treated with ferric ammonium citrate (FAC) and an inhibitor of glutathione synthesis (BSO). FRDA cells have long been known to be sensitive to treatment with iron, BSO, or a combination of both. Moreover, the ferroptosis inhibitor SRS11-92 decreased the cell death associated with frataxin knockdown in healthy human fibroblasts. Taken together, these data suggest activation of the ferroptosis pathway in FRDA cells and, consequently, that ferroptosis inhibitors could be used as therapeutics in Friedreich ataxia, Oleic acid is an eighteen carbon monounsaturated omega-9 fatty acid, that has been reported to inhibit imidazole-ketone-erastin induced ferroptosis in G-401 cells through an uncharacterized mechanism. Oleic acid was tested in primary, patient-derived fibroblasts, as well as mouse cells with FRDA-associated mutations treated with FAC and BSO and found that it was efficacious in rescuing cell viability.

Oleic acid has been shown to interact with PPAR-γ and promote PGC1-α transcription, but increased PGC1-α expression was unable to rescue viability in cells treated with FAC and BSO. A commercial inhibitor of lipoxygenase-15 (Lox15) enzymatic activity was efficacious in the FAC+BSO assay, but the optimized analog did not inhibit Lox15 activity the assay.

Example 1

Oleic Acid (OA) Rescues the Viability of Murine FRDA Fibroblasts Treated with FAC BSO, or Treated with the Ferroptosis Inducer Erastin Whether oleic acid (OA) rescues FRDA cells from erastin-induced ferroptosis was tested using the murine 1154F fibroblast model. Treatment with 5 μM erastin for 48 h resulted in 44% cell survival. Oleic acid at 20 μM, 10 μM, and 5 μM increased survival in a dose-dependent manner to 65%, 55%, and 49% respectively (FIG. 1A). Whether OA was efficacious in rescuing murine 1154F fibroblasts treated with FAC+BSO was then tested Treatment with FAC+BSO decreased cell viability to 40% of control cells (FIG. 1B). Adding 16 μM linoleic acid further decreased cell viability to 30% of control cells, whereas oleic acid at the same concentration doubled cell survival. Stearic acid (C18:0) had no effect. The $EC_{50}$ of oleic acid in the FAC+BSO in mouse fibroblasts assay was 23 μM (FIG. 1C).

The methyl and ethyl esters, amide, methyl amide and hydroxamic acid of this long-chain saturated natural fatty acid were tested to evaluate the effect of masking the carboxylic acid (See Tables below). It is possible the esters are acting as pro-drugs, delivering the free carboxylic acid, and the less effective amide results from less efficient conversion to the carboxylic acid.

A variety of other, commercially available unsaturated C18 fatty acids were also evaluated, including cis-vaccenic acid (C18:1 Δ11), petrosenilic acid (C18:1 Δ6) gadoleic (C20:1 Δ9 ω11) erucic (C22:1 Δ13 ω9) and palmitoleic (C16:1 Δ9 ω7). The efficacy of these compounds was comparable to oleic acid when used at 40 μM (see Table 1 below), indicating that the position of the olefin had no effect on activity. Elaidic acid, the trans isomer of oleic acid, was somehow effective at 160 μM but slightly toxic at 40 μM (see table below).

Consistent with previous data, polyunsaturated fatty acid as γ-linolenic acid (C18:3 Δ6,9,12) resulted in increased cell death following FAC+BSO treatment. On the other hand, short chain unsaturated fatty acids like capric acid and lauric acid were consistently inactive in the assay with the exception of palmitic acid, which has been reported to be a strong inducer of apoptosis (see table below).

The table below summarizes the results obtained: the compounds were tested at 40 μM in the mouse fibroblast I154F cell lines where 40 μM oleic acid doubled survival of cells treated with iron and BSO. The activity of each compound was then comprised between 1 (oleic acid) and 0.5 (no rescue). A value <0.5 indicated that the compound was toxic.

TABLE 1

| Parent | R | Relative to Oleic Acid | | |
|---|---|---|---|---|
| Oleic Acid C18:1 Δ9 cis | OH | 1.03 ± 0.04 | | |
| | OMe | 0.95 ± 0.12 | | |
| | OEt | 0.77 ± 0.18 | | |
| | NH2 | 0.79 ± 0.13 | | |
| | NHMe | n.a. | Not comm | OA330 |
| | NHOH | 1.04 ± 0.04 | Not comm | OA310 |
| | | (10 μM) | | |

TABLE 1-continued

| Parent | R | Relative to Oleic Acid |
|---|---|---|
| Elaidic Acid C18:1 Δ9 trans | | 0.30 ± 0.08 |
| Cis-Vaccenic Acid C18:1 Δ11 | | 1.00 ± 0.08 |
| Petrosenilic Acid C18:1 Δ6 | | 0.74 ± 0.04 |
| γ-linolenic Acid C18:3 Δ6,9,12 | | 0.16 ± 0.02 |
| Gadoleic acid C20:1 Δ9 cis | | 0.77 ± 0.16 |
| Erucic add C22:1 Δ9 | | 0.93 ± 0.07 |
| Heptadecenoic acid | | 0.83 ± 0.05  0.7 ± 0.05 (20 μM) |
| Palmitoleic Acid | | 0.77 ± 0.03  0.73 ± 0.04 (20 μM) |
| Lauric Acid | | 0.47 ± 0.12 |
| Stearic Acid | | 0.50 ± 0.06 |
| Capric Acid | | 0.49 ± 0.09 |
| Myristic Acid (C14) | | 0.11 ± 0.02 |
| Palmitic Acid (C16) | | 0.18 ± 0.07 |

In addition, trifluoromethyl ketones and alcohol analogs of oleic acid, palmitoleic acid and heptadecanoic acid were prepared. The synthesis of the trifluromethyl ketones of oleic acid and palmitoleic acid has been previously described. The synthesis of the heptadecanoic acid analog occurred via a similar method. To prepare the racemic alcohols, the acid was converted to the aldehyde, then treated with TMS-CF3. In the case of oleic acid derivatives, chiral alcohols were prepared from the trifluoromethyl ketone, via chiral reduction using each enantiomer of CBS reagent to provide the enantiomerically pure alcohols. Of these, both oleic acid analogs were active, but the other derivatives were devoid of activity.

Separating the enantiomers of OA-200 led to the R and S enantiomer, and a differentiation of activity. The activity resides in the (R) enantiomer, while the (S) enantiomer is inactive. Example 8 has a synthesis for preparing the S and R enantiomers of OA200 and OA210.

Example 2

To test the efficacy of the above compounds, they were tested at least at two different concentrations using human FRDA fibroblast line GM4078 treated with FAC and BSO and the change in survival compared to cells treated with 40 μM oleic acid was measured Table 2 has the results of the compounds tested at 40 μM. Compounds OA200 and OA210 were slightly toxic at that concentration but a dose response revealed that they were, in fact, active at lower concentrations down to 5 μM.

TABLE 2

| Compound | Parent | Relative to Oleic Acid | |
|---|---|---|---|
| HA-210 | Heptadecanoic acid | 0.35 ± 0.02 | |
| [rac]-HA-200 | Heptadecanoic acid | 0.56 ± 0.03 | |
| OA-210 | Oleic Acid | 0.52 ± 0.13 | 10 μM |
| [rac]-OA-200 | Oleic Acid | 0.67 ± 0.17 | 10 μM |
| (R)- | | | |
| (S)- | | | |
| PA-200 | Palmetoleic acid | 0.57 ± 0.05 | |
| [rac]-PA-210 | Palmetoleic acid | 0.39 = 0.03 | |
| OA-50 (epoxide) | Oleic acid | 0.15 ± 0.02 | OA-50 |
| OA-81 (diol) | Oleic acid | 0.14 ± 0.03 | OA-81 |

TABLE 2-continued

| | Parent | Relative to Oleic Acid | |
|---|---|---|---|
| (structure) | Oleic acid | 0.05 ± 0.02 | OA-90 |
| (structure) | Oleic acid | 0.24 ± 0.04 | OA-95 |

Example 3

Figure 2:
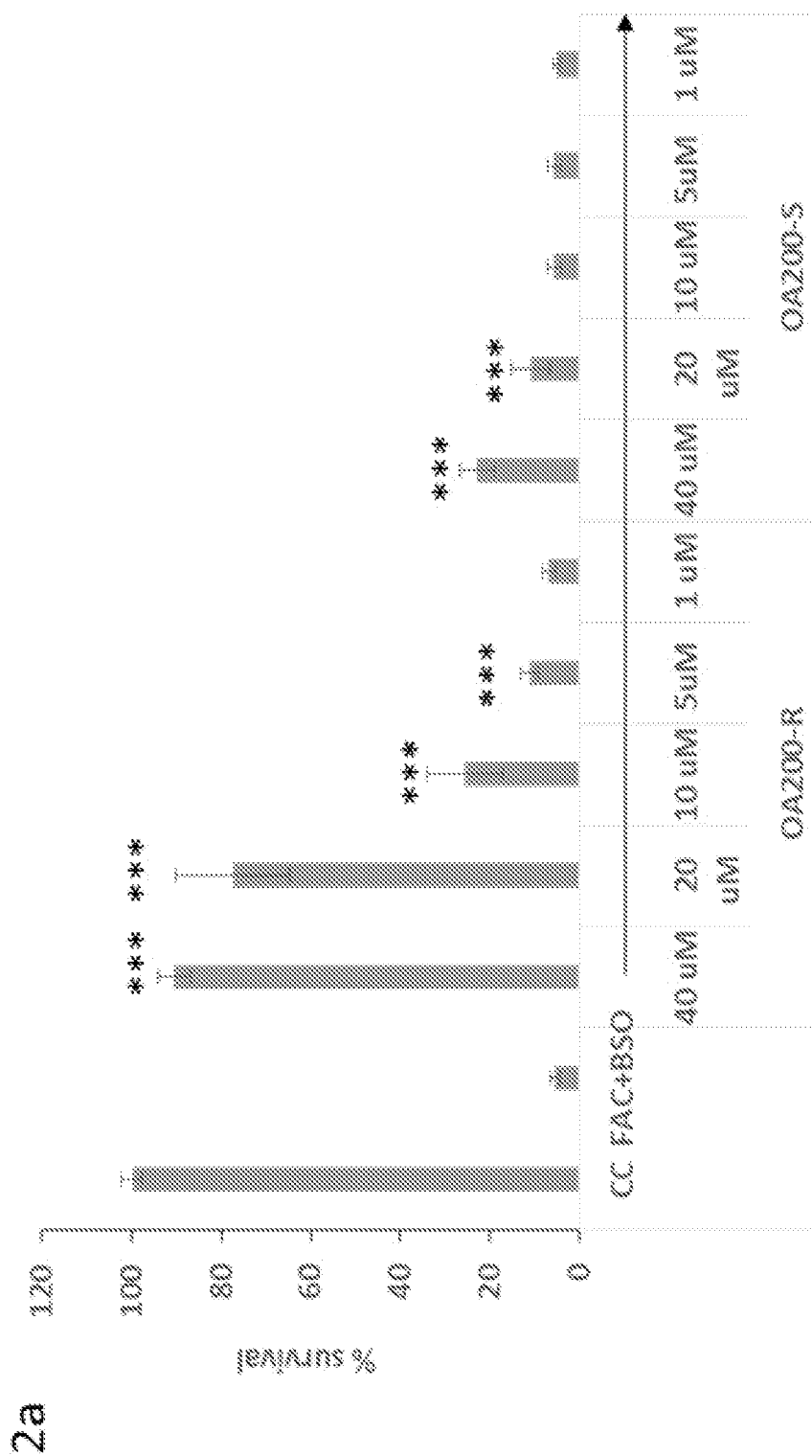
FIG. 2. The stereo-specific activity of the two enantiomers OA200R and OA200S was confirmed using the immortalized human fibroblasts 3665-T cells, a more severe model of FRDA. Treatment with FAC and BSO resulted in 95% cell death. OA200R at 40 µM, 20 µM and 10 µM brought up survival to 95% and 77% and 25%, respectively, whereas at 40 µM and 20 µM the S-isomer only increased survival to 22% and 10% and was inefficacious at 5 µM.
Figure 2:
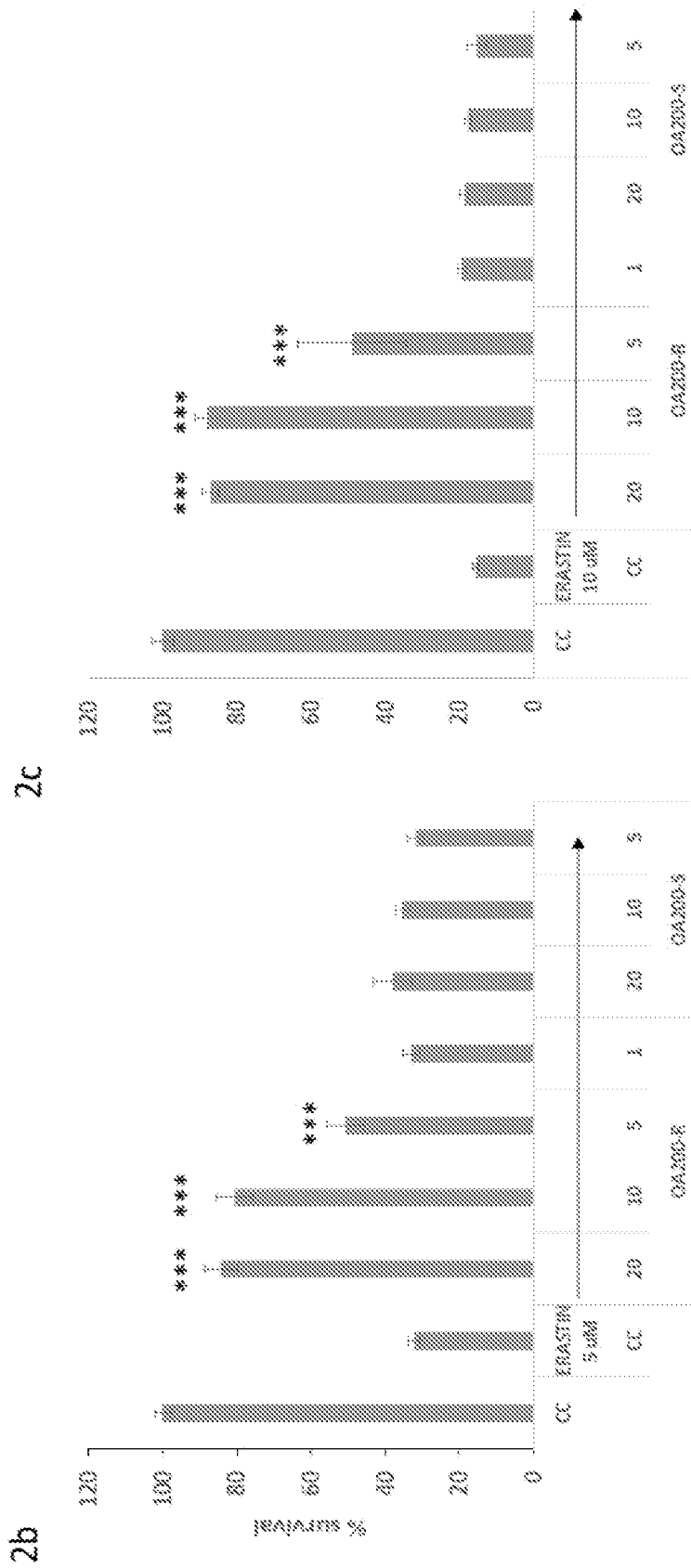

Stereospecific activity of the two enantiomers was confirmed using the immortalized human fibroblasts 3665-T cells, a more severe model of FRDA. Treatment with FAC and BSO resulted in 95% cell death. OA200R at 40 µM, 20 µM and 10 µM brought up survival to 95% and 77% and 25%, respectively, whereas at 40 µM and 20 µM the S-isomer only increased survival to 22% and 10% and was inefficacious at 5 µM. (FIG. 2A).

Example 4

Whether OA200R could rescue human FRDA fibroblasts 3816 treated with erastin was tested Treatment with erastin at 5 µM resulted in 32% cell survival after 48 h. Addition of OA200R at 5 µM was sufficient to increase survival to 50% (1.5 fold) and at 10 µM and 20 µM survival went up to 80 and 84% (2.5 and 2.6 fold) respectively (FIG. 2B). The S-isomer showed no activity between 20 and 5 µM. In parallel experiments, OA raised survival to 1.5 fold when used at 20 µM, consistent with the data shown in FIG. 2A.

The experiment was repeated at different time points: treatment with 10 µM erastin for 24 h resulted in 85% cell death. Under these conditions, oleic acid at 40 µM did not rescue cell viability, whereas OA200R increased survival to 48% at 5 µM and 87% and 88% when used at 10 or 20 µM, respectively. The S-isomer again was inactive at any concentration (FIG. 2C).

Oleic acid, as well as other fatty acids of different length and degree of saturation, binds and activates the peroxisome proliferator-activated receptor gamma (PPAR-γ), a key regulator of glucose and lipid metabolism, which up-regulates PGC1-α, among other targets. Pioglitazone, a PPAR-γ agonist is a thiazolidinedione used to treat type-2 diabetes. It was briefly considered as an FRDA therapeutic as PGC1-α levels are paradoxically downregulated in FRDA cells but its cardio-toxicity precluded its further use in FRDA patients. Human FRDA fibroblasts GM3816 were treated with 10 µM pioglitazone and increased PGC1-α expression was measured starting at 48 h. The expression doubled at 96 h, a time frame sufficient for PGC1-α to have an effect in a typical FAC+BSO experiment, whereas 16 µM oleic acid increased PGC1-α expression only 1.4 fold after 96 h. But pioglitazone did not affect survival of cells treated with FAC+BSO, ruling out that increased survival in the assay is mainly mediated by PGC1-α upregulation.

Figure 5:
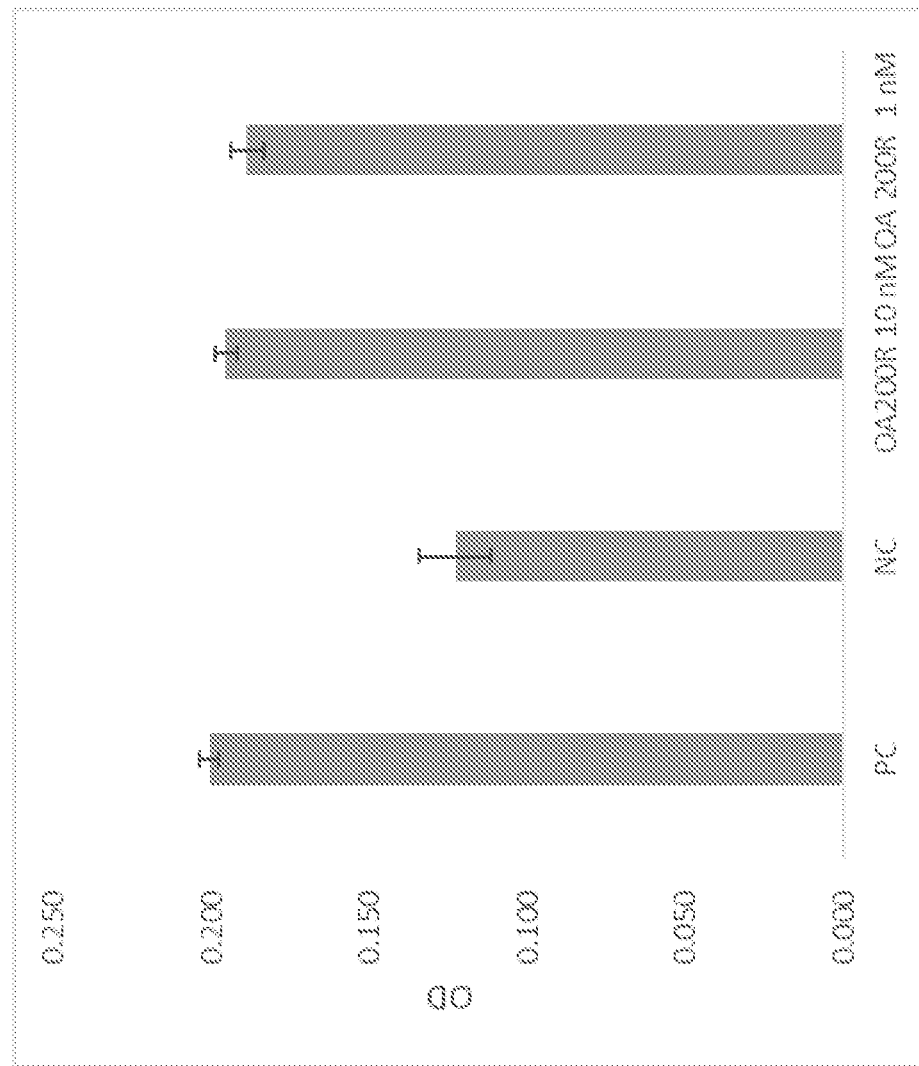
FIG. 5. Oleic acid derivative 200R does not inhibit lipoxygenases. PC Positive Control (no inhibitor added); NC. Negative Control (inhibitor added); OA200R at two (10 nM and 1 nM) concentrations. OA200R does not inhibit at these concentrations, in these conditions.

Oleic acid has been reported to inhibit soybean lipoxygenase, as well as human 15-lipoxygenase, by binding an allosteric site. Lipoxygenases (Lox) are non-hence containing enzymes that catalyze formation of hydroperoxides using unsaturated fatty acids containing a cis,cis, 1-4 pentadiene system as substrate, thus increasing the lipid peroxide load of the cells. Whether OA200R was inhibiting lipoxygenase activity was tested using an in vitro assay. Although solubility problems precluded the use of high concentrations, OA200R at 1 nM and 10 nM did not affect Lox enzymatic activity (FIG. 5).

Example 5

Figure 3:
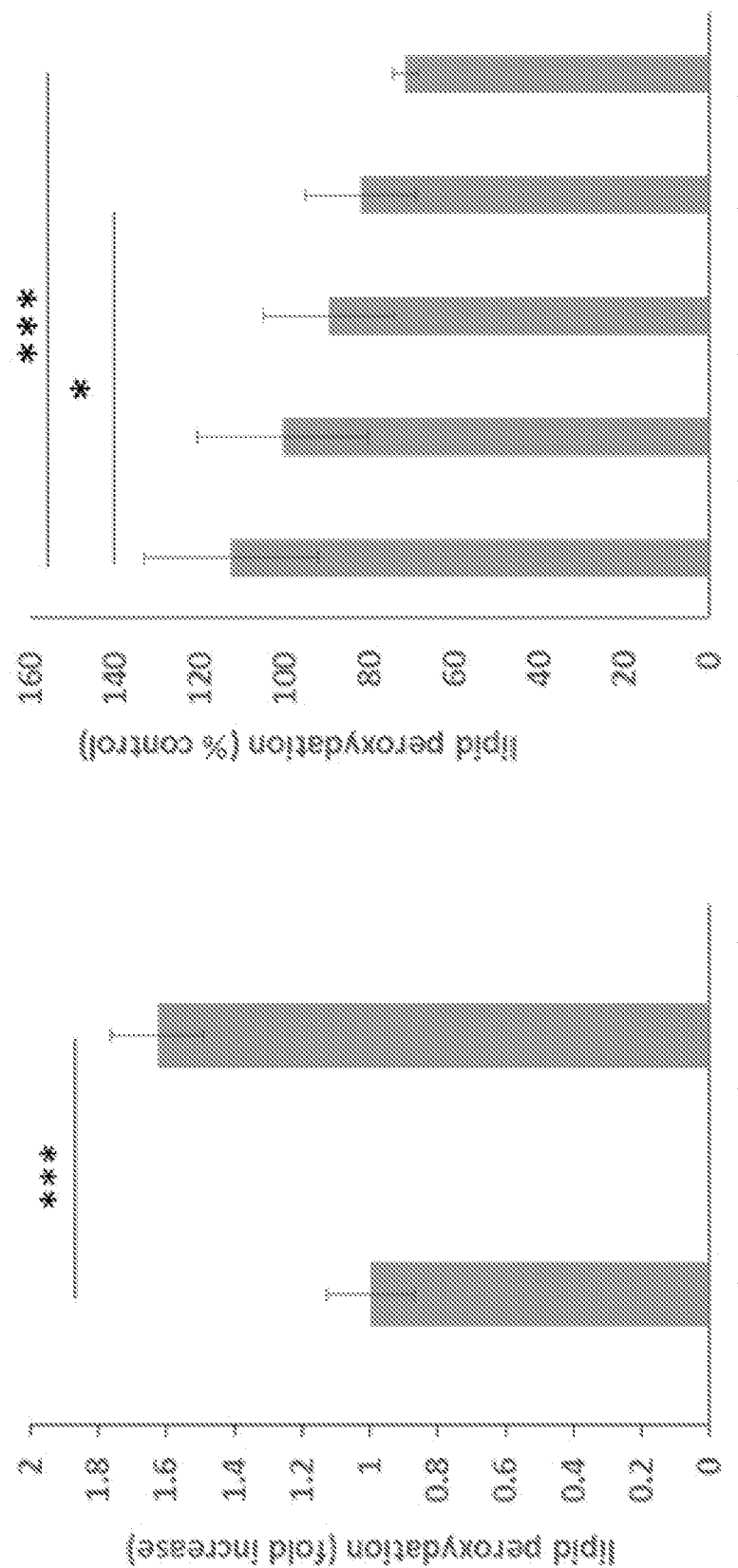
FIG. 3. It was previously shown that ferroptosis inhibitors, considered to be radical trapping antioxidant (RTA), were efficacious in the FAC+BSO assay and could reduce lipid peroxidation. Basal level of lipid peroxides in murine fibroblast I154F cells were tested compared to the parental line 2F1 and a detectable higher level of lipid peroxides in the cells containing a missense frataxin was found (FIG. 3A). Treating I154F cells with OA200R reduced lipid peroxidation in a dose-dependent manner and reach statistical significance at 5 μM.

Ferroptosis inhibitors, considered to be radical trapping antioxidant (RTA), were shown to be efficacious in the FAC+BSO assay and could reduce lipid peroxidation. The basal level of lipid peroxides was tested in the murine fibroblast I154F cells compared to the parental line 2F1 and a detectable higher level of lipid peroxides was found in the cells containing a missense frataxin (FIG. 3A). Treatment of I154F cells with OA200R reduced lipid peroxidation in a dose-dependent manner and reached statistical significance at 5 µM (FIG. 3B).

Example 6

Figure 4:
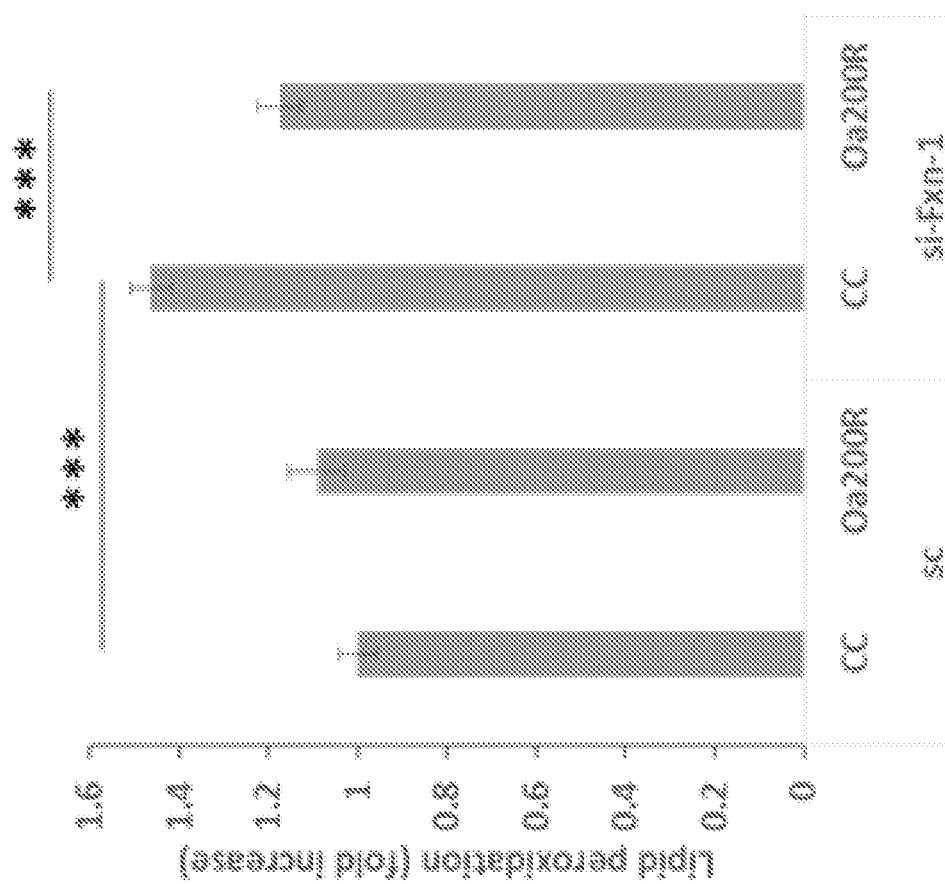
FIG. 4. As previously shown, knocking-down frataxin in human fibroblasts results in increased lipid peroxidation, which could be easily measured when cells were also treated with the ferroptosis inducer RSL-3. To test whether OA200R is efficacious in the knock-down system, an immortalized myoblast cell line was transfected with a frataxin siRNA or a scrambled siRNA control. A 65% protein loss over 4 days and a statistically significant increase of lipid peroxidation (1.4 fold) compared to cells transfected with a scrambled control were achieved Treating OA200R at 5 μM every 48 h post transfection resulted in 20% decreased lipid peroxidation.

Knocking-down frataxin in human fibroblasts results in increased lipid peroxidation, which could be easily measured when the cells were also treated with the ferroptosis inducer RSL-3. To test whether OA200R would be efficacious in the knock-down system, an immortalized myoblast cell line was transfected with a frataxin siRNA or a scrambled siRNA control. A 65% protein loss was achieved over 4 days and a statistically significant increase of lipid peroxidation (1.4 fold) compared to the cells transfected with a scrambled control. Treatment with OA200R at 5 µM every 48 h post transfection resulted in 20% decreased lipid peroxidation (FIG. 4).

Example 7—Synthesis of Racemic OA-200

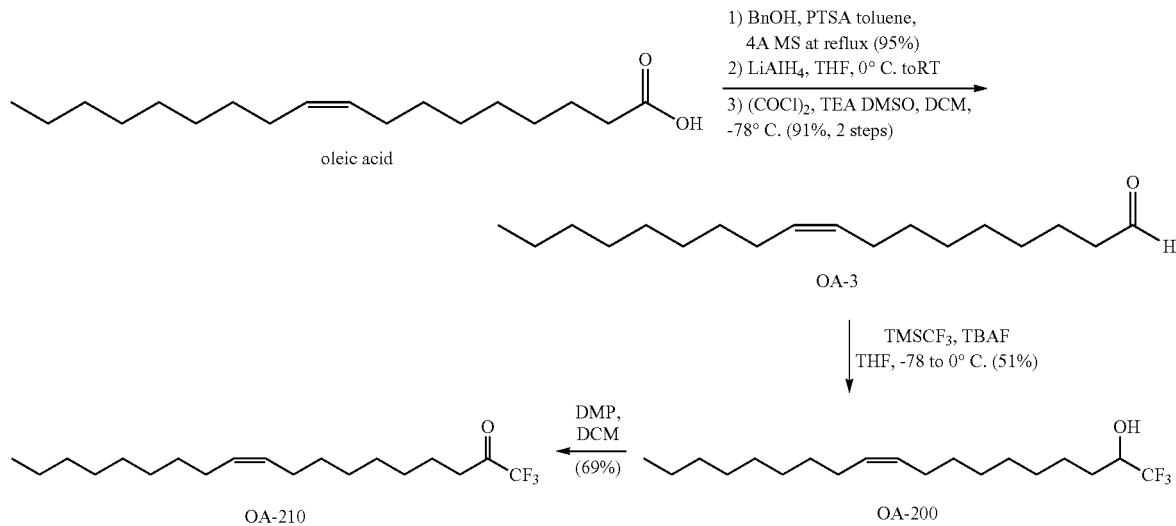

Synthesis of Benzyl Oleic Acid

To a solution of oleic acid (17.8 g, 63.0 mmol) in toluene (300 mL) were added benzyl alcohol (8.5 mL, 82.0 mmol), p-toluenesulfonic acid monohydrate (0.61 g, 3.2 mmol), 4 Å molecular sieves (20 grams) and the resultant solution was stirred for at reflux for 24 hours. TLC analysis of the reaction shows complete disappearance of starting material. The reaction mixture was then quenched with water/methanol 9/1 (300 mL), extracted with hexanes (300 mL), washed with water (3×600 mL), dried over MgSO$_4$, and evaporated under vacuum. The product was purified by column chromatography (silica gel, step gradient from 9:1 hexane/ethyl acetate to 100% ethyl acetate) to afford compound benzyl oleic acid (22.3 g, 95%) as a yellowish oil, $^1$H NMR (500 MHz, CDCl$_3$) δ 7.36 (m, 5H), 5.36 (m, 2H), 5.13 (s, 2H), 2.36 (t, =7.45 Hz, 2H), 2.02 (m, 4H), 1.66 (t, =6.9 Hz, 2H), 1.29 (m, 20H), 0.90 (t, J=6.6 Hz, 3H). $^{13}$C NMR (125 MHz, CDCl$_3$) δ 174.0, 136.5, 130.3, 130.1, 128.9, 128.5, 66.4, 34.7, 32.2, 30.1, 30.0, 29.9, 29.7, 29.5, 29.4, 29.4, 27.6, 27.5, 25.3, 23.0, 14.4, HRESIMS [M+Na]$^+$ m/z 395.2928 (calcd for C$_{25}$H$_{40}$O$_2$Na, 395.2926).

Synthesis of OA-3

To a 0° C. solution of benzyl oleic acid (20.0 g, 53.7 mmol) in tetrahydrofuran (400 mL) was added LiAlH$_4$ (4.1 g, 107.4 mmol) and the resultant solution was slowly warmed up to room temperature and stirred for 3 hours. TLC analysis of the reaction shows complete disappearance of starting material. The reaction mixture was then cooled down to 0° C. and quenched with a dropwise addition of water (10 mL). A saturated solution of Rochelle's salt (400 mL) was then added and the resultant solution was stirred overnight. The two layers were separated and the top layer was diluted with ethyl acetate (300 mL), washed with water (300 mL×3), dried over MgSO$_4$, and evaporated under vacuum. The primary alcohol (crude product) was used in the next step without further purification. To a −78° C. solution of oxalyl chloride (9.1 mL, 107.4 mmol) in dichloromethane (400 mL) was slowly added dimethylsulfoxide (19.1 mL, 268.5 mmol) and the resultant solution was stirred for 20 minutes. A solution of the primary alcohol (crude product) in dichloromethane (100 mL) was then added dropwise and the reaction mixture was stirred for at −78° C. for 45 minutes, Triethylamine (30.0 mL, 214.8 mmol) was added dropwise and the solution was stirred for 30 additional minutes. TLC analysis of the reaction shows complete disappearance of starting material. The reaction mixture was then quenched with a saturated solution of NaHCO$_3$ (500 mL), washed with water (500 mL), washed with saturated CuSO$_4$.5H$_2$O (500 mL), washed with water again (500 mL), dried over MgSO$_4$, and evaporated under vacuum. The product was purified by column chromatography (silica gel, step gradient from 9:1 hexane/ethyl acetate to 100% ethyl acetate) to afford OA-3 (11.6 g, 81%, 2 steps) as a yellowish oil, $^1$H NMR (500 MHz, CDCl$_3$) δ 9.73 (s, 1H), 5.32 (s, 2H), 2.39 (t, J=6.1 Hz, 2H), 1.99 (m, 6H), 1.60 (m, 2H), 1.26 (m, 19H), 0.86 (t, 6.4 Hz, 3H). $^{13}$C NMR (125 MHz, CDCl$_3$) δ 203.1, 130.3, 129.9, 44.2, 32.2, 30.1, 30.0, 29.8, 29.6, 29.6, 29.4, 29.3, 27.5, 27.4, 23.0, 22.4, 14.4, HRESIMS [M+H]$^+$ m/z 267.2682 (calcd for C$_{18}$H$_{35}$O, 267.2688).

Methods for the Synthesis of OA-200, PA-200, HA-200

To a −78° C. of OA-3 (1.0 g, 3.76 mmol) in tetrahydrofuran (50 mL) were added TMSCF$_3$ (0.61 mL, 4.13 mmol), a solution of TBAF in tetrahydrofuran (1.88 mL, 1.88 mmol, 1M) and the resultant solution was warmed up to 0° C. and stirred for 5 minutes. TLC analysis of the reaction shows complete disappearance of starting material. The reaction mixture was quenched with H$_2$O (50 mL), extracted with ethyl acetate (50 mL), washed with H$_2$O (3×50 mL), dried over MgSO$_4$, and evaporated under vacuum, To a solution of crude product in tetrahydrofuran (50 mL) was added a solution of TBAF in tetrahydrofuran (3.76 mL, 3.76 mmol, 1M) and the resultant solution was stirred for 30 minutes at room temperature. TLC analysis of the reaction shows complete disappearance of starting material. The reaction mixture was quenched with water (50 mL), extracted with ethyl acetate (100 mL), washed with water (3×100 mL), dried over MgSO$_4$, and evaporated under vacuum. The product was purified by column chromatography (silica gel, step gradient from 9:1 hexane/ethyl acetate to 100% ethyl acetate) to afford OA-200 (0.64 g, 51%) as a colorless oil. OA-200: $^1$H NMR (500 MHz, CDCl$_3$) δ 5.31 (m, 2H), 3.90 (bs, 1H), 2.27 (bs, 1H), 2.02 (m, 4H), 1.70 (m, 1H), 1.58 (m. 2H), 1.29 (m, 21H), 0.88 (t, 5.7 Hz, 3H). $^{13}$C NMR (125 MHz, CDCl$_3$) δ 130.4, 130.1, 125.6 (m), 70.9 (m), 32.3, 31.9, 30.1, 30.0, 29.9, 29.9, 29.7, 29.6 29.5, 29.5, 27.6, 27.5, 25.3, 23.0, 23.0, 14.5. CIMS m/z 336.2643 (calcd for $C_{19}H_{35}F_3O$, 336.2640).

Example 8—Synthesis of R- and S-Enantiomers

Synthesis of (R,Z)-1,1,1-trifluorononadec-10-en-2-ol and (S,Z)-1,1,1-trifluorononadec-10-en-2-ol Synthesis of (Z)-1,1,1-trifluorononadec-10-en-2-one (OA-210)

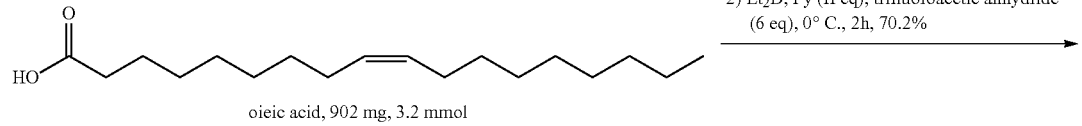

oleic acid, 902 mg, 3.2 mmol

1) DCM, (COCl)$_2$ (3 eq), dark, 26° C., 3h
2) Et$_2$D, Py (II eq), trifluoroacetic anhydride (6 eq), 0° C., 2h, 70.2%

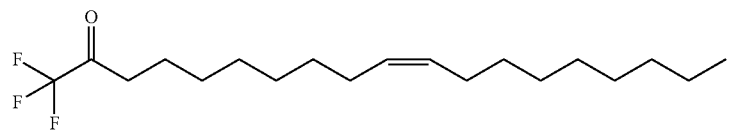

OA-210, 700 mg, 2.2 mmol

To a solution of oleic acid (902 mg, 12 mmol, 1.0 equiv) in anhydrous CH$_2$Cl$_2$ (15.0 mL) at 0° C. under nitrogen atmosphere oxalyl chloride (0.796 mL, 9.4 mmol, 3.0 equiv) was added slowly. The reaction mixture was warmed to 25° C. and was stirred in the dark for 3 h. before the solvent was removed in vacuum. The above crude mixture was dissolved in anhydrous Et$_2$O (22.0 mL) and trifluoroacetic anhydride (2.64 mL, 19.0 mmol, 6.0 equiv), and pyridine (2.0 mL, 25.0 mmol, 8.0 equiv) were added successively at 25° C., and the resulting solution was stirred for 45 min before being cooled to 0° C. The reaction was monitored by TLC and TLC of the final reaction mixture showed complete disappearance of starting material. Then the reaction was quenched with the addition of H$_2$O (30.0 mL), and the aqueous layer was extracted with CH$_2$Cl$_2$ (3×30.0 mL). The organic layers were dried over anhydrous Na$_2$SO$_4$, filtered, and concentrated in vacuum. The resulting crude product was purified using silica gel chromatography (Combi flash Rf; 1.0% Et$_3$N in 5% EtOAc-hexane) to afford (Z)-1,1,1-trifluorononadec-10-en-2-one (OA-21.0, 700 mg, 70%) as a yellow color oil: $^1$H NMR (600 MHz, CDCl$_3$): δ 5.41-5.28 (m, 2H), 2.70 (t, =7.2 Hz, 2H), 2.06-1.97 (m, 4H), 1.72-1.62 (m, 2H), 1.38-1.22 (m, 20H), 0.92-0.85 (m, 3H) ppm.

Synthesis of (Z)-1,1,1-trifluorononadec-10-en-2-ol (OA-200-RS)

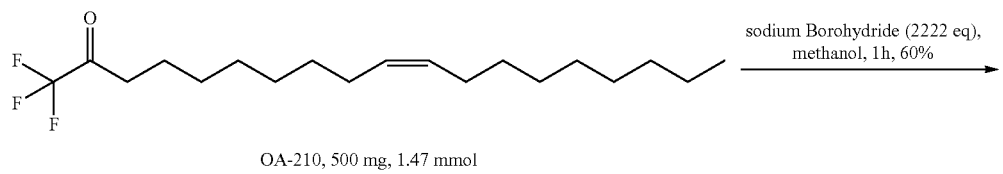

OA-210, 500 mg, 1.47 mmol sodium Borohydride (2222 eq), methanol, 1h, 60%

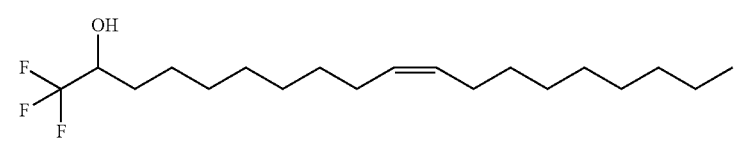 [SMILES: CCCCCCCC/C=C\CCCCCCC[C@@H](O)C(F)(F)F]

OA-200-RS, 283 mg, 60 mmol

To a solution of (Z)-1,1,1-trifluorononadec-10-en-2-one (OA-210, 500 mg. 1.47 mmol, 1.0 equiv) in methanol (20 mL) under nitrogen atmosphere at 0° C. was added sodium borohydride (111.6 mg, 2.95 mmol, 2.0 equiv) and the resulting reaction mixture was stirred at 0° C. for 1 h. The reaction was monitored by TLC and TLC of the final reaction mixture showed complete disappearance of starting material. The reaction was quenched with the addition of $H_2O$ (30.0 mL) at 0° C. then the aqueous layer was extracted with ethyl acetate (3×30.0 mL), The organic layers were dried over anhydrous $Na_2SO_4$, filtered, and concentrated in vacuum. The resulting crude product was purified using silica gel chromatography (Combi flash 5% EtOAc-hexane) to yield (Z)-1,1,1-trifluorononadec-10-en-2-ol (OA-200-RS, 283 mg, 60%) as a yellow color oil: $^1H$ NMR (600 MHz, $CDCl_3$): δ 5.38-5.32 (m, 2H), 3.94-3.88 (m, 1H), 2.06-1.97 (m, 4H), 1.72-1.66 (m, 1H), 1.63-1.54 (m, 2H), 1.43-1.19 (m, 22H), 0.92-0.82 (m, 3H) ppm.

Synthesis of (S,Z)-1,1,1-trifluorononadec-10-en-1-ol (OA-200-S)

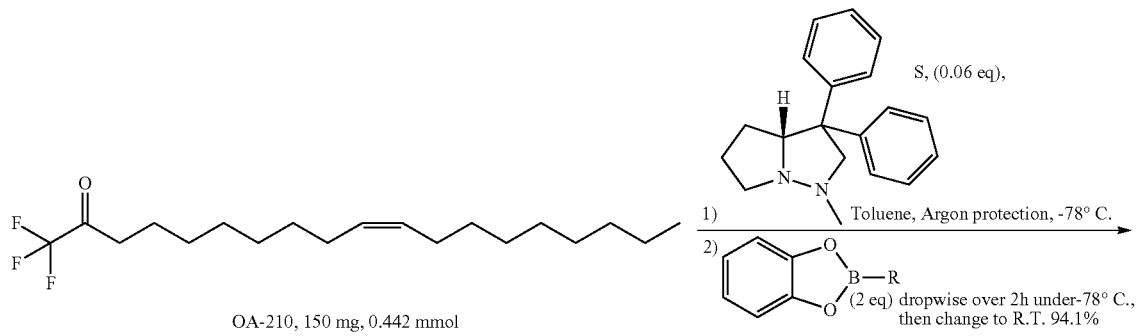

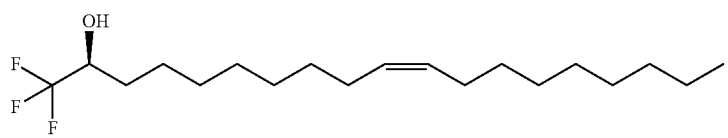

OA-200-(R), 140 mg, 0.446 mmol O.R. -14.4

To a solution of (Z)-1,1,1-trifluorononadec-10-en-2-one (OA-210; 150 mg, 0.442 mmol, 1.0 equiv) in toluene (4.0 mL) was added (3Ar)-1-methyl-3,3-diphenyl-3a,4,5,6-tetrahydro-2H-pyrrolo[2,1-e]azaborole (0,022 mL, 0.022 mmol, 0.05 equiv) and the resultant solution was stirred under the protection of argon at −78° C. Then 1,3,2-benzodioxaborole (0.885 mL, 0.885 mmol, 2.0 equiv) was added dropwise over 2 h at −78° C., and the reaction mixture was stirred at room temperature for 1 h. The reaction was monitored by TLC and TLC of the final reaction mixture showed complete disappearance of starting material. The reaction was quenched with the addition of $H_2O$ (30.0 mL) at 0° C. and the aqueous layer was extracted with ethyl acetate (3×30.0 mL). The organic layers were dried over anhydrous $Na_2SO_4$, filtered, and concentrated in vacuum. The resulting crude product was purified using silica gel chromatography (Combi flash Rf, 5% EtOAc-hexane) to produce (S,Z)-1,1,1-trifluorononadec-10-en-2-ol (OA-200-S, 140 mg, 94%) as a yellow color oil, $[α]_D$=−14.4 (c=0.8200, $CHCl_3$): $^1H$ NMR (600 MHz, $CDCl_3$): δ 5.38-5.32 (m, 2H), 3.94-3.88 (m, 1H), 2.06-1.97 (m, 4H), 1.72-1.66 (m, 1H), 1.63-1.54 (m, 2H), 1.43-1.19 (m, 22H), 0.92-0.82 (m, 3H) ppm.

Synthesis of (R,Z)-1,1,1-trifluorononadec-10-en-2-ol (OA-200-R)

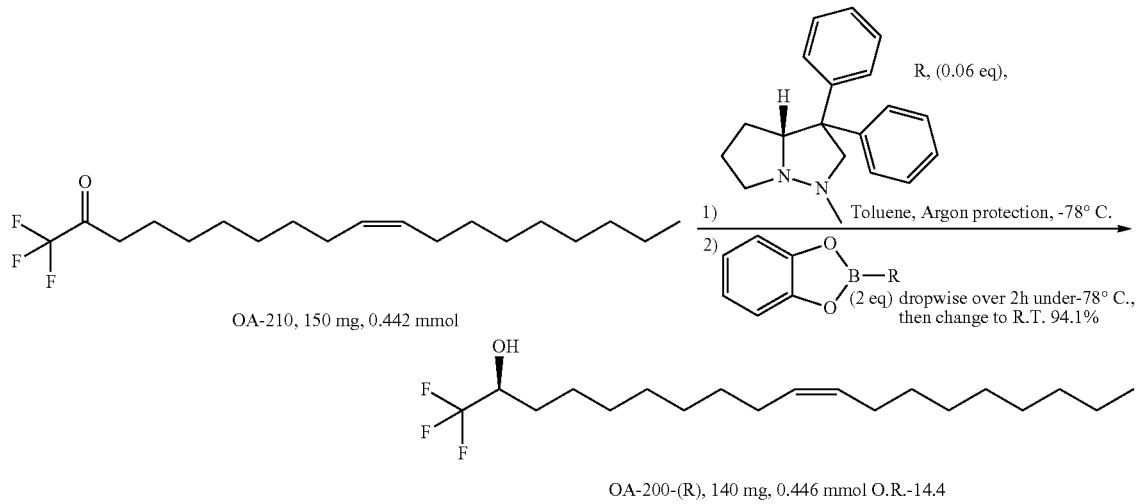

To a solution of (Z)-1,1,1-trifluorononadec-10-en-2-one (OA-210, 150 mg; 0.442 mmol, 1.0 equiv) in toluene (4.0 mL) was added (3aS)-1-methyl-3,3-diphenyl-3a,4,5,6-tetrahydro-2H-pyrrolo[2,1-e]azaborole (0.022 mL, 0.022 mmol, 0.05 equiv) and the resultant solution was stirred under the protection of argon at −78° C. Then 1,3,2-benzodioxaborole (0.885 mL, 0.885 mmol, 2.0 equiv) was added dropwise over 2 h at −78° C., and the reaction mixture was stirred at room temperature for 1 h. The reaction was monitored by TLC and TLC of the final reaction mixture showed complete disappearance of starting material. The reaction was quenched with the addition of $H_2O$ (30.0 mL) at 0° C. and the aqueous layer was extracted with ethyl acetate (3×30.0 mL). The organic layers were dried over anhydrous $Na_2SO_4$, filtered, and concentrated in vacuum. The resulting crude product was purified using silica gel chromatography (Combi flash Rf, 5% EtOAc-hexane) to produce (R,Z)-1,1,1-trifluorononadec-10-en-2-ol (OA-200-R, 140 mg, 94%) as a yellow color oil. $[\alpha]_D$=+14.4 (c=0.8200, $CHCl_3$): $^1H$ NMR (600 MHz, $CDCl_3$): δ 5.38-5.32 (m, 2H), 3.94-3.88 (m, 1H), 2.06-1.97 (m, 4H), 1.72-1.66 (m, 1H), 1.63-1.54 (m, 2H), 1.43-1.19 (m, 22H), 0.92-0.82 (m, 3H) ppm.

We have thus identified, inter alia, OA200R, an oleic acid-derivative which is efficacious in cellular models of Friedreich ataxia and ferroptosis. The data are consistent with OA200R being a radical trapping antioxidant, which may or may not be localized in the lipid bilayer. It has been proposed that oleic acid supplementation could simply "decrease the abundance" of polyunsaturated fatty acid in the membrane and the same could be said for OA200R. However, if this was the case, saturated fatty acids should be efficacious and they are not. Identification of a eutomer also points to a stereo-specific step that is required for increased potency, suggesting that OA200R could be integrated as a membrane constituent, perhaps as derivative, raising questions about its processing, localization and cell compartmentalization.

Preparation of Compounds of the Invention

The practitioner has a well-established literature of small molecule chemistry to draw upon, in combination with the information contained herein, for guidance on synthetic strategies, protecting groups, and other materials and methods useful for the synthesis of the compounds described herein.

The various references cited herein provide helpful background information to prepare compounds similar to those described herein or relevant intermediates, as well as information on formulation, uses, and administration of such compounds which may be of interest.

Moreover, the practitioner is directed to the specific guidance and examples provided herein relating to various exemplary compounds and intermediates thereof.

The compounds described and their preparation can be understood further by the examples that illustrate some of the processes by which they are prepared or used. It will be appreciated, however, that these examples do not limit the invention. Variations, now known or further developed, are considered to fall within the scope of this invention as described herein and as hereinafter claimed.

Any available techniques can be used to make or prepare the compounds described herein or compositions including them. For example, a variety of solution phase synthetic methods such as those discussed in detail here may be used. Alternatively or additionally, the compounds may be prepared using any of a variety combinatorial techniques, parallel synthesis and/or solid phase synthetic methods known in the art.

It will be appreciated that a variety of the compounds can be synthesized according to the methods described herein, Starting materials and reagents used in preparing these compounds are either available from commercial suppliers such as Aldrich Chemical Company (Milwaukee, WI), Bachem (Torrance, CA), Sigma (St. Louis, MO), or are prepared by methods well known to a person of ordinary skill in the art following procedures described in such references as Fieser and Fieser 1991, "Reagents for Organic Synthesis", vols 1-17, John Wiley and Sons, New York, NY, 1991; Rodd 1989 "Chemistry of Carbon Compounds", vols. 1-5 and supps, Elsevier Science Publishers, 1989; "Organic Reactions", vols 1-40, John Wiley and Sons, New York, NY, 1991; March 2001, "Advanced Organic Chemistry", $5^{th}$ ed, John Wiley and Sons, New York, NY; and Larock 1990, "Comprehensive Organic Transformations: A Guide to Functional Group Preparations", 2$^{nd}$ ed, VCH Publishers. These schemes are merely illustrative of methods by which compounds described here can be synthesized, and various modifications to them can be made and will be suggested to one of ordinary skill in the art having regard to this disclosure.

The starting materials, intermediates, and compounds described herein may be isolated and purified using conventional techniques, including filtration, distillation, crystallization, chromatography, and the like. They may be characterized using conventional methods, including physical constants and spectral data.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A compound represented by Formula I

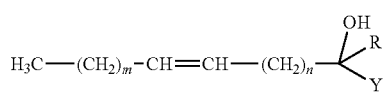

wherein
R is H or $C_1$-$C_6$ alkyl;
m is an integer from 3 to 8;
n is an integer from 3 to 8; and
Y is $CF_3$ or $CCl_3$,
or an optical isomer thereof.

2. The compound of claim 1, wherein Y is $CF_3$.
3. The compound of claim 1, wherein R is H.
4. The compound of claim 1, wherein R is $CH_3$ or $CH_3CH_2$.
5. The compound of claim 1, wherein said compound is represented by Formula IA or by Formula IB

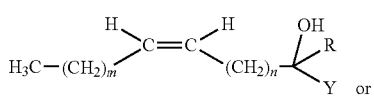

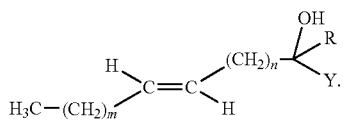

6. The compound of claim 5, wherein said compound has an S configuration.
7. The compound of claim 5, wherein said compound has an R configuration.
8. The compound of claim 5, wherein the weight ratio of the R isomer to the S isomer is from 70:30 to 99.99:0.01.
9. The compound of claim 5, wherein the weight ratio of the S isomer to the R isomer is from 70:30 to 99.99:0.01.
10. The compound of claim 5, wherein the compound is a racemic mixture.
11. The compound of claim 1, wherein said compound is

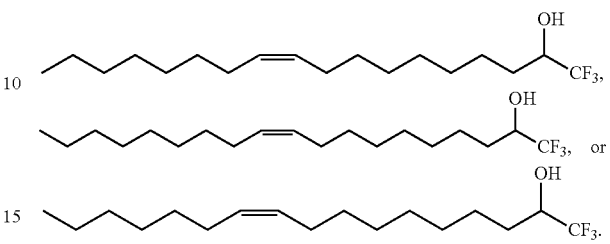

12. The compound of claim 1, wherein said compound is

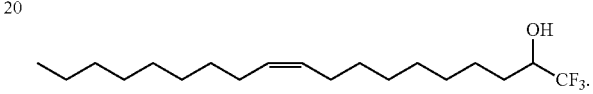

13. The compound of claim 1, wherein said compound is

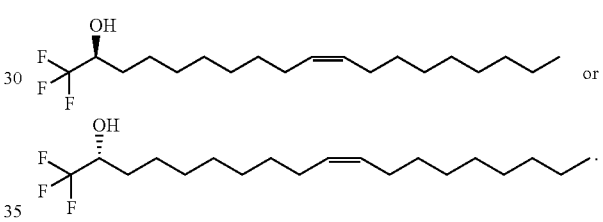

14. A pharmaceutical composition comprising a compound according to claim 1, and a pharmaceutically acceptable carrier.

15. The pharmaceutical composition of claim 14, wherein said compound is

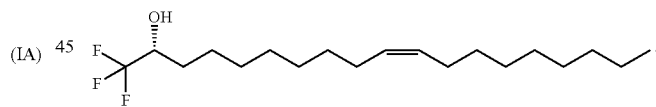

16. A method of treating Friedreich ataxia in a subject, comprising administering to the subject an effective amount of a compound having the following formula:

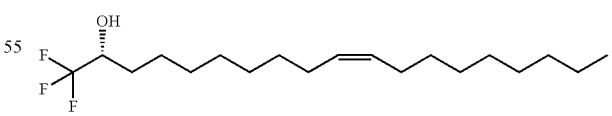

or a pharmaceutical composition thereof.

* * * * *